(12) United States Patent
Greaves et al.

(10) Patent No.: US 7,303,591 B2
(45) Date of Patent: *Dec. 4, 2007

(54) COMPOSITION COMPRISING AT LEAST ONE MIXED DYE COMPRISING AT LEAST TWO CHROMOPHORES OF (HETERO) AROMATIC NITRO OR CYCLIC AZINE TYPE, DYEING PROCESS, AND MIXED DYES

(75) Inventors: Andrew Greaves, Montevrain (FR); Hervé David, Joinville le Pont (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 340 days.

This patent is subject to a terminal disclaimer.

(21) Appl. No.: 11/066,453

(22) Filed: Feb. 28, 2005

(65) Prior Publication Data

US 2005/0235434 A1    Oct. 27, 2005

Related U.S. Application Data

(60) Provisional application No. 60/568,273, filed on May 6, 2004.

(30) Foreign Application Priority Data

Feb. 27, 2004  (FR) .................................. 04 50382

(51) Int. Cl.
*A61K 7/13* (2006.01)
(52) U.S. Cl. ........................ 8/405; 8/406; 8/407; 8/410; 8/411; 8/423; 8/426; 8/437; 8/565; 8/566; 8/567; 8/568; 8/570; 8/573; 8/574; 8/608; 534/269.4; 548/301.7
(58) Field of Classification Search .................... 8/405, 8/406, 407, 410, 411, 423, 426, 437, 565, 8/566, 567, 568, 570, 573, 574, 608; 534/269.4; 548/301.7
See application file for complete search history.

(56) References Cited

U.S. PATENT DOCUMENTS

| | | | |
|---|---|---|---|
| 3,423,427 A | 1/1969 | Cescon et al. | |
| 3,642,823 A | 2/1972 | Raue et al. | |
| 3,652,556 A | 3/1972 | Küthau et al. | |
| 3,995,088 A | 11/1976 | Garner et al. | |
| 4,054,718 A | 10/1977 | Garner et al. | |
| 4,165,434 A | 8/1979 | Schafer et al. | |
| 4,670,385 A | 6/1987 | Babb et al. | |
| 4,823,985 A | 4/1989 | Grollier et al. | |
| 4,873,320 A | 10/1989 | Springer et al. | |
| 5,094,688 A | 3/1992 | Eckstein et al. | |
| 5,097,034 A | 3/1992 | Eckstein | |
| 5,139,997 A | 8/1992 | Bach et al. | |
| 5,214,140 A | 5/1993 | Bach et al. | |
| 5,708,151 A * | 1/1998 | Mockli .................... | 534/608 |
| 6,297,362 B1 | 10/2001 | Kunde et al. | |
| 6,468,316 B1 | 10/2002 | Genet et al. | |
| 6,485,527 B1 | 11/2002 | Prechtl et al. | |
| 6,592,634 B1 | 7/2003 | Reichert et al. | |
| 6,607,563 B2 | 8/2003 | Ohashi et al. | |

FOREIGN PATENT DOCUMENTS

| | | |
|---|---|---|
| BE | 702 239 | 8/1967 |
| DE | 1 254 118 | 11/1967 |
| DE | 3 335 956 A1 | 4/1985 |
| DE | 198 45 640 | 4/2000 |
| EP | 1 153 598 A2 | 11/2001 |
| FR | 2 586 913 | 3/1987 |
| GB | 822 846 | 11/1959 |
| GB | 1 047 796 | 11/1966 |
| GB | 1 199 641 | 7/1970 |
| JP | 1-313569 | 12/1989 |
| JP | 2-292370 | 12/1990 |
| JP | 63-165460 | 7/1998 |
| JP | 2000-204026 | 7/2000 |
| JP | 2000-281921 | 10/2000 |
| JP | 2001-316231 | 11/2001 |
| JP | 2002-12533 | 1/2002 |
| JP | 2005-500283 | 1/2005 |
| WO | WO 02/78596 A2 | 10/2002 |
| WO | WO 02/078596 A2 | 10/2002 |
| WO | WO 03/018021 A1 | 3/2003 |
| WO | WO 03/029359 | 4/2003 |
| WO | WO 03/030909 A1 | 4/2003 |

OTHER PUBLICATIONS

STIC Search Report dated Mar. 15, 2007.*
English language Abstract for JP 1-313569 from Patent Abstracts of Japan (1990).
English language Abstract for JP 2-29370 from Patent Anstracts of Japan (1990).
Von Alfred Kreutzberger et al., "2,4,6-Gemischtfunktionell substituierte 1,3,5-Triazine," *Chemiker Zeitung* 111(7-8):241-5, 1987.
English language Derwent Abstract of DE 1254118 (1967).
English language Derwent Abstract of DE 3335956, dated Apr. 18, 1985.
French Search Report, dated Oct. 7, 2004.
Robert M. Schelkum, et al., Subtype-Selective N-Methyl-D-aspartate Receptor Anatagonists: Benzimidazalone and Hydantoin as Penol Replacements, *Journal of Medicinal Chemistry*, 43(9):1892-97, 2000.

* cited by examiner

*Primary Examiner*—Eisa Elhilo
(74) *Attorney, Agent, or Firm*—Finnegan, Hendeson, Farabow, Garrett & Dunner LLP

(57) ABSTRACT

A dye composition comprising at least one mixed dye comprising at least two chromophore chosen from azine and (hetero)aromatic nitro compounds, optionally associated with at least one chromophore chosen from methine and carbonyl compounds; a process for dyeing keratin fibers, for example, human keratin fibers, such as the hair, using the composition, a multi-compartment device comprising the composition; and the abovementioned mixed dyes.

37 Claims, No Drawings

COMPOSITION COMPRISING AT LEAST ONE MIXED DYE COMPRISING AT LEAST TWO CHROMOPHORES OF (HETERO) AROMATIC NITRO OR CYCLIC AZINE TYPE, DYEING PROCESS, AND MIXED DYES

This application claims benefit of U.S. Provisional Application No. 60/568,273, filed May 6, 2004, the contents of which are incorporated herein by reference. This application also claims benefit of priority under 35 U.S.C. § 119 to French Patent Application No. 0450382, filed Feb. 27, 2004, the contents of which are also incorporated by reference.

Disclosed herein is a dye composition comprising at least one mixed dye comprising at least two chromophores chosen from cyclic azine and (hetero)aromatic nitro compounds, and also to a process for dyeing keratin fibers, for example, human keratin fibers, using the composition. Also disclosed herein are mixed dyes per se.

It is known practice to dye keratin fibers, for example, human hair with dye compositions comprising direct dyes. These compounds may be colored or coloring molecules that have affinity for the fibers. It is known practice, for example, to use nitrobenzene dyes; anthraquinone dyes; nitropyridine dyes; and azo, xanthene, acridine, azine, and triarylmethane dyes.

These dyes can be applied to the fibers, optionally in the presence of an oxidizing agent, if it is desired to obtain simultaneous lightening of the fibers. Once the action time has elapsed, the fibers may be rinsed, optionally washed, and dried.

The colorations resulting from the use of direct dyes are temporary or semi-permanent colorations. The nature of the interactions that bind the direct dyes to the keratin fiber and their desorption from the surface and/or from the core of the fiber are at least two factors that may be responsible for their weak dyeing power and their relatively poor wash-fastness or perspiration-fastness.

An additional difficulty may also arise, associated with the fact that, in order to obtain a particular color, it is necessary in most cases, if not all cases, to mix several dyes. However, each dye may not have the same affinity for the fiber, which is reflected either by heterogeneous colorations or by changing of the color over time, for example after washing the fibers at least one time, exposure to sunlight, etc.

In one embodiment, at least one of the aims of the present inventors is to provide direct dyes that do not have at least some of the drawbacks of the existing direct dyes.

For example, at least one aim is to provide direct dyes that can afford varied shades without any problem of changing of the color over time.

At least some of these aims and others may be achieved by the present disclosure, one embodiment of which is a dye composition comprising, in a medium that is suitable for dyeing keratin fibers, for example, human keratin fibers, at least one mixed dye comprising at least two different chromophores; wherein at least one of the chromophores is chosen from cyclic azine and (hetero)aromatic nitro compounds, optionally associated with at least one chromophore chosen from methine and carbonyl compounds; wherein the at least two chromophores are linked together via at least one linker that stops delocalization of the electrons of each of the chromophores, with the following exception: the dye composition is not a composition comprising a mixed dye comprising two chromophores one of which is a benzene nitro compound and the other an anthraquinone or benzene nitro compound; wherein the two chromophores are connected by a nitrogen atom through a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals. In one embodiment, the dye composition does not comprise, mixed dyes comprising two chromophores, wherein one of which is a benzene nitro compound and the other a benzene nitro or anthraquinone compound, wherein the two chromophores are connected via a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals. Further, the dye composition does not comprise compounds of the following formulae:

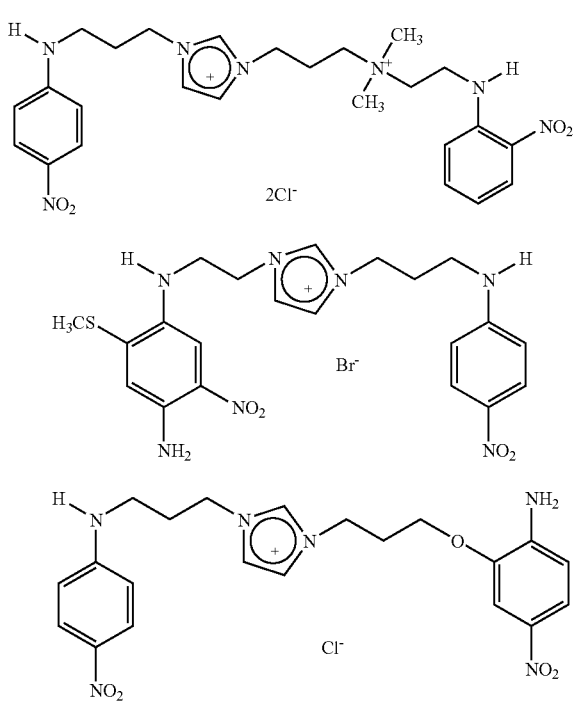

Further disclosed herein is a process for dyeing keratin fibers, for example, human keratin fibers, comprising applying at least one dye composition disclosed herein, leaving the at least one dye composition to act for a time that is sufficient to obtain the desired coloration, optionally rinsing the fibers, optionally washing and rinsing fibers, and drying the fibers or leaving the fibers to dry.

Further disclosed herein is a mixed dye comprising at least two different chromophores; wherein at least one of the chromophores is chosen from cyclic azine and (hetero) aromatic nitro compounds, optionally associated with at least one chromophore chosen from methine and carbonyl compounds, wherein the at least two different chromophores are linked together via at least one linker that stops delocalization of the electrons of each of the chromophores, with the following exceptions: the mixed dye is not a mixed dye having two chromophores one of which is a benzene nitro compound and the other an anthraquinone or benzene nitro compound; wherein the two chromophores are connected by a nitrogen atom through a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals and the mixed dye is not chosen from compounds of the following formulae:

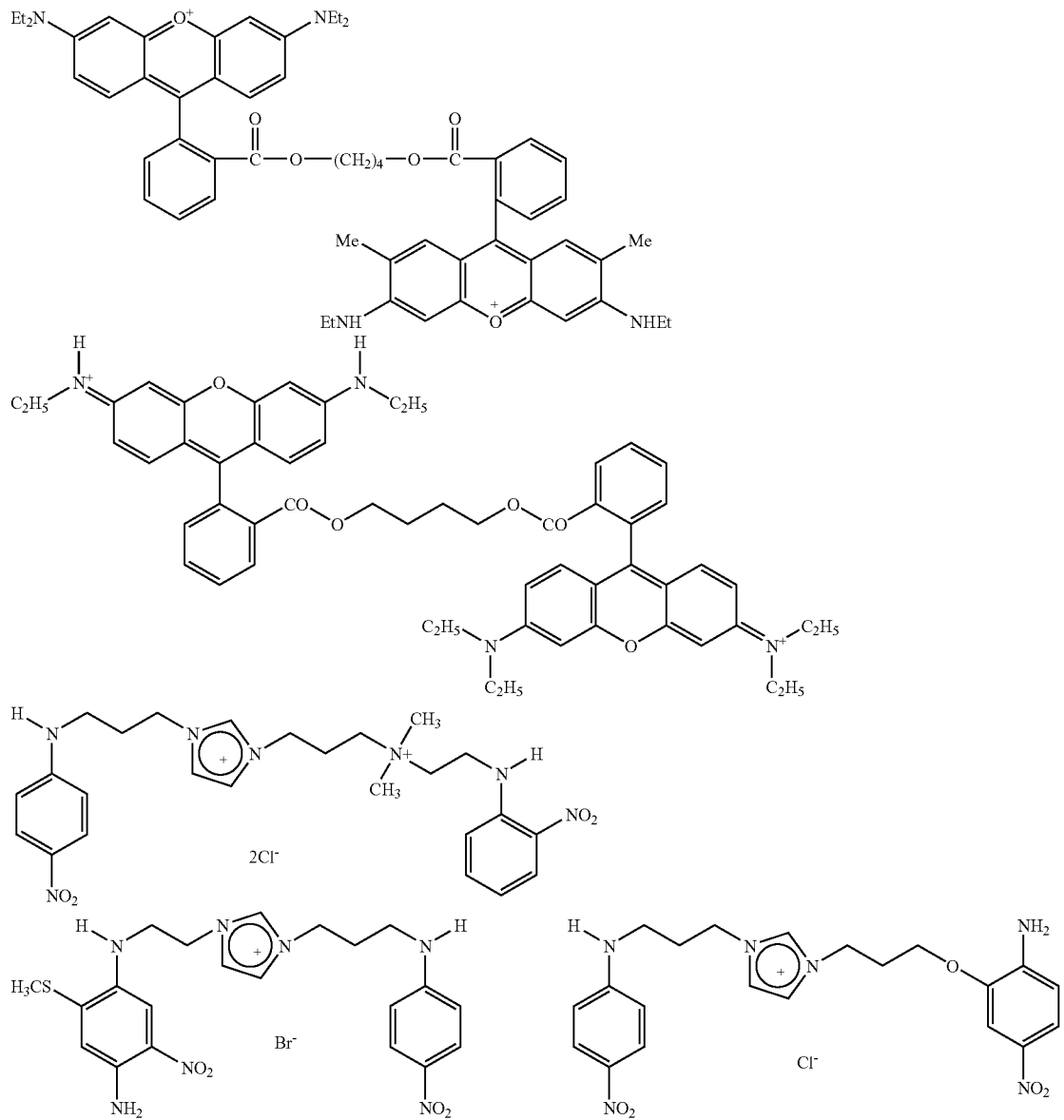

It has been found that the dye composition disclosed herein may make it possible to obtain strong, light-stable colors that are resistant to bad weather, to washing and to perspiration, and show good fastness over time.

However, other characteristics and advantages of the dyeing composition disclosed herein will emerge more clearly on reading the description and the examples that follow.

In the text hereinbelow, and unless otherwise indicated, the expression "substituted alkyl, substituted aryl (or aromatic) or substituted heteroaryl (or heteroaromatic) radical" means an alkyl, aryl or heteroaryl radical bearing at least one entity chosen from a hydroxyl radical; halogen atoms, such as chlorine and fluorine; linear and branched, substituted and unsubstituted $C_1$-$C_8$ and, for example, $C_1$-$C_4$ alkoxy radicals; linear and branched, substituted and unsubstituted monohydroxyalkoxy radicals, wherein the alkyl portion is chosen from $C_1$-$C_8$ alkyl radicals and, for example, $C_1$-$C_4$ alkyl radicals; linear and branched, substituted and unsubstituted $C_2$-$C_8$ polyhydroxyalkoxy radicals and, for example, $C_2$-$C_4$ polyhydroxyalkoxy radicals; amino radicals substituted with at least one substituent, which may be identical or different, chosen from linear and branched, substituted and unsubstituted $C_1$-$C_8$ alkyl radicals and, for example, $C_1$-$C_6$ alkyl radicals and optionally substituted, $C_6$ aryl radicals; thiol radicals; linear and branched, substituted and unsubstituted $C_1$-$C_8$ alkylthio radicals and, for example, $C_1$-$C_4$ alkylthio radicals; carboxylic radicals in acid or salified form (for example, with an alkali metal or a substituted or unsubstituted ammonium); linear and branched, substituted and unsubstituted alkoxycarbonyl radicals, wherein the alkyl portion is chosen from $C_1$-$C_8$ alkyl radicals and, for example, $C_1$-$C_4$ alkyl radicals; alkylamide radicals, wherein the alkyl portion is chosen from linear and branched, substituted and unsubstituted $C_1$-$C_8$ alkyl radicals and, for example, $C_1$-$C_4$ alkyl radicals; alkylcarbamyl radicals wherein the alkyl portion is chosen from linear and branched, substituted and unsubstituted $C_1$-$C_8$ alkyl radicals and, for example, $C_1$-$C_4$ alkyl radicals; nitro radicals; sulfonyl radicals; linear and branched, substituted and unsubstituted $C_1$-$C_8$ alkylsulfonyl radicals and, for example, $C_1$-$C_4$ alkylsulfonyl radicals; sulfonylamino radicals; and alkylsulfonylamido radicals wherein the alkyl portion is chosen from linear and branched, substituted and unsubstituted $C_1$-$C_8$ alkyl radicals and, for example, $C_1$-$C_4$ alkyl radicals.

It should be recalled that a heteroaromatic or heteroaryl radical corresponds to an aromatic radical wherein at least one of the carbon atoms is replaced with a hetero atom chosen, for example, from nitrogen, oxygen, and sulfur.

Furthermore, when it is indicated that the alkyl or aryl radical or the alkyl or aryl portion of a radical is substituted with another radical this means that the alkyl or aryl radical or alkyl or aryl portion of the radical, itself, comprises at least one substituent chosen from a hydroxyl group; amino groups; amino groups substituted with at least one substituent, which may be identical or different, chosen from linear and branched $C_1$-$C_4$ alkyl radicals, optionally bearing at least one hydroxyl group; and linear and branched $C_1$-$C_4$ alkoxy radicals optionally bearing at least one hydroxyl group.

When mention is made of amino radicals bearing two substituents chosen from optionally substituted alkyl radicals, it is understood that the alkyl radicals can also form, with the nitrogen atom to which they are attached, a 5- or 6-membered ring, at least one of the carbon atoms of which may be replaced with at least one hetero atom chosen from nitrogen, oxygen, and sulfur atoms.

Furthermore, unless otherwise indicated, the limits delimiting the extent of a range of values are included in this range of values.

In addition, because the at least one mixed dye disclosed herein may be cationic, their counterion(s) may be chosen from cosmetically acceptable mineral and organic anions. Examples of mineral anions include halides, such as chlorides and bromides; hydroxides; sulfates; hydrogen sulfates; carbonates; and hydrogen carbonates.

Examples of organic anions include acetate; citrate; tartrate; alkyl sulfates, wherein the linear or branched alkyl portion is chosen from $C_1$-$C_6$ alkyl radicals, for example, methosulfate and ethosulfate ions; alkylsulfonates, wherein the linear or branched alkyl portion is chosen from $C_1$-$C_6$ alkyl radicals; arylsulfonates wherein the aryl portion, for example, phenyl, is optionally substituted with at least one $C_1$-$C_4$ alkyl radical.

The at least one mixed dye present in the dye composition disclosed herein will first be described.

As indicated previously, the at least one mixed dye comprises at least two different chromophores; wherein at least one of the chromophores is chosen from cyclic azine and (hetero)aromatic nitro compounds, optionally associated with at least one chromophore chosen from methine and carbonyl compounds; wherein the chromophores are linked together via at least one linker that stops delocalization of the electrons of each of the chromophores.

In one embodiment, at least one of the chromophores of the mixed dye bears at least one cationic charge.

As used herein, the term "chromophore" means a radical derived from a dye, i.e. a radical of a molecule that absorbs in the visible range from 400 to 800 nm. It should be further noted that this absorbance of the dye does not require either any prior oxidation of the dye, or any association with (an)other chemical species.

When it is mentioned that the chromophores are different, this means that at least two of them, and, for example, all of them, differ in their chemical structure. Such chromophores may be derived from different families or from the same family provided that they have different chemical structures. For example, the chromophores may be chosen from the same family of dyes but differ in the chemical structure of the radicals constituting them.

In one embodiment, the at least one mixed dye comprises two to four chromophores and, for example, two to three chromophores.

It should be noted that when the at least one mixed dye comprises more than two chromophores, at least one of these chromophores is different from the other(s).

In one embodiment, the mixed dye comprises two chromophores and in a further embodiment, those chromophores are the same.

In another embodiment, the chromophore(s) is(are) cationic and is(are) chosen from chromophores comprising at least one quaternized nitrogen atom.

Furthermore, the at least one cationic charge may or may not be engaged in a ring.

Moreover, as indicated above, at least one of the chromophores of the mixed dye comprises at least one cationic charge and, in one embodiment, only one cationic charge.

For example, according to this variant, each of the chromophores comprises at least one cationic charge, and, in one embodiment, only one cationic charge.

In another embodiment, the at least one mixed dye has an overall cationic charge, under the conditions of use of the at least one mixed dye.

As indicated above, the at least one mixed dye may comprise at least one chromophore chosen from cyclic azine compounds.

In one embodiment, the cyclic azine compounds are radicals derived from dyes chosen from azine, xanthene, thioxanthene, fluorindine, acridine, (di)oxazine, (di)thiazine, and pyronine.

Examples of cyclic azine compounds include the compounds of formula (I) below, and tautomeric forms thereof:

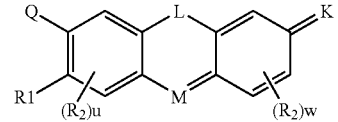

wherein:

L is chosen from hetero atoms, for example, oxygen and sulfur; NH; and N—$R_3$;

M is chosen from hetero atoms, for example, oxygen, sulfur and nitrogen; $N^+$—$R_3$; CH; and C—$R_4$;

Q and K, which may be identical or different, are each chosen from a hydroxyl radical; amino radicals; amino radicals substituted with at least one substituent, which may be identical or different, chosen from linear and branched $C_1$-$C_8$ alkyl radicals, optionally bearing at least one entity chosen from a hydroxyl radical, optionally substituted aryl radicals, and optionally substituted ($C_1$-$C_8$)alkylaryl radicals; an $N^+(R_5)_t$ ammonium radical wherein t equals to 2 for K and to 3 for Q; $R_5$, which may be identical or different, is chosen from a hydrogen atom; linear and branched $C_1$-$C_8$ alkyl radicals, optionally bearing at least one hydroxyl group; optionally substituted aryl radicals; ($C_1$-$C_8$)alkylaryl radicals, wherein the aryl portion is optionally substituted;

optionally substituted linear and branched $C_1$-$C_8$ alkyl radicals; and optionally substituted linear and branched $C_1$-$C_8$ alkoxy radicals, provided that Q and K do not simultaneously represent a $N^+(R_5)_t$ ammonium radical;

$R_1$ and $R_2$, which may be identical or different, are each chosen from a hydrogen atom; optionally substituted linear and branched $C_1$-$C_8$ alkyl radicals; amino radicals; amino radicals optionally substituted with at least one substituent, which may be identical or different, chosen from linear and branched, optionally substituted $C_1$-$C_8$ alkyl radicals, optionally substituted phenyl radicals; and halogen atoms, for example, chlorine and fluorine;

provided that when Q is a substituted or unsubstituted amino radical or a hydroxyl group, $R_1$ is chosen from alkylamino and alkoxy radicals forming, with the nitrogen or oxygen atom of the radical Q, a 6-membered ring, optionally fused with an aromatic radical, wherein the aromatic radical is optionally substituted with at least one substituent chosen from amino radicals and amino radicals, optionally substituted with at least one substituent, which may be identical or different, chosen from optionally substituted linear and branched $C_1$-$C_8$ alkyl radicals and optionally substituted phenyl radicals;

$R_3$ and $R_4$, which may be identical or different, are each chosen from linear and branched $C_1$-$C_8$ alkyl radicals, which are optionally substituted, for example, with at least one substituent chosen from a hydroxyl radical; linear and branched $C_1$-$C_8$ alkoxy radicals; amino radicals; and amino radicals substituted with at least one substituent, which may be identical or different, chosen from linear and branched $C_1$-$C_8$ alkyl radicals, optionally bearing at least one hydroxyl radical;

$R_3$ and $R_4$, which may be identical or different, may also be chosen from aryl radicals, for example, a $C_6$ aryl radical, which is optionally substituted, for example, with at least one substituent chosen from linear and branched $C_1$-$C_8$ alkyl radicals; a hydroxyl radical; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; halogen atoms, for example, chlorine and fluorine; a nitro radical; and a cyano radical. In one embodiment, $R_3$ and $R_4$, which may be identical or different, are each chosen from linear $C_1$-$C_4$ alkyl radicals and optionally substituted aryl radicals;

u is equal to 2; and w is equal to 3.

Further, the chromophore is linked to the linker via one of the radicals $R_1$, $R_2$, $R_3$, $R_4$ or $R_5$, or via a ring. In this case, the radical borne by the ring represents a single bond between the chromophore and the linker.

In one embodiment, the cyclic azine chromophores are chosen from compounds of the formulae below, and also, where appropriate, tautomeric forms thereof:

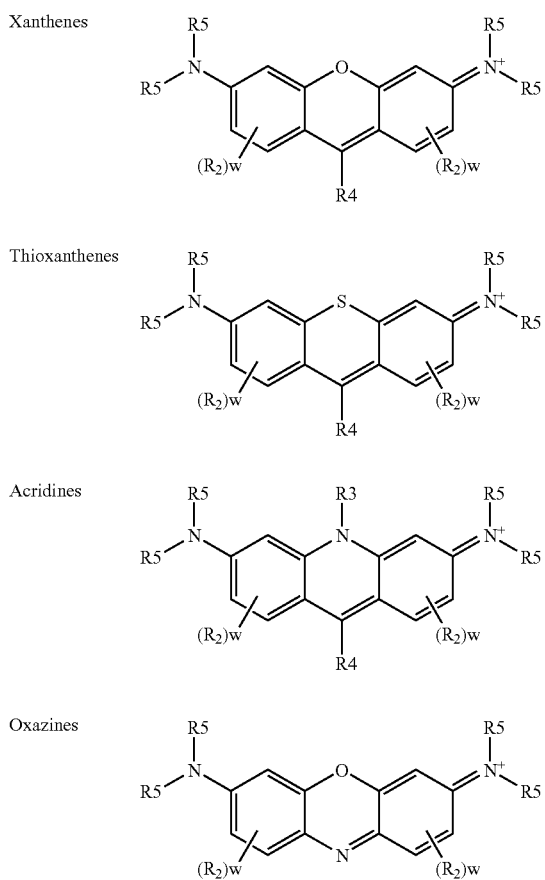

-continued

Dioxazines

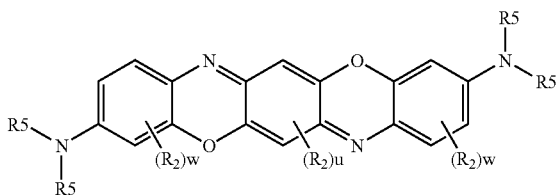

Thiazines

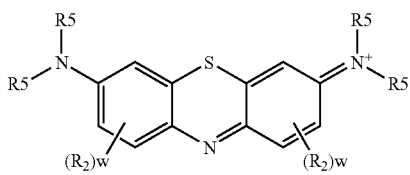

Phenazines

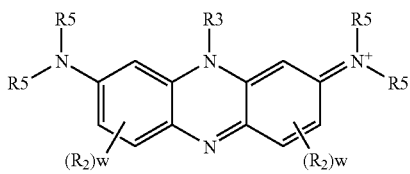

wherein the radicals and u and w have been defined previously.

The chromophore is furthermore linked to the linker via one of the radicals $R_2$, $R_3$, $R_4$ or $R_5$, or via a ring. In this case, the radical borne by the ring represents a single bond between the chromophore and the linker.

In one embodiment, the at least one mixed dye may comprise at least one chromophore chosen from (hetero) aromatic nitro compounds.

Examples of (hetero)aromatic nitro compounds include the compounds corresponding to formulae (II) and (III) below, and tautomeric forms thereof:

Benzene-based

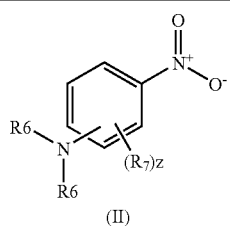

(II)

Pyridine-based

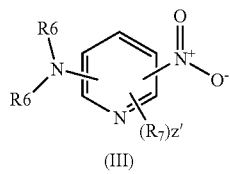

(III)

wherein:

$R_6$, which may be identical or different, is chosen from a hydrogen atom; linear and branched $C_1$-$C_8$ alkyl radicals, optionally bearing at least one hydroxyl group; optionally substituted aryl radicals; ($C_1$-$C_8$)alkylaryl radicals, wherein the aryl portion is optionally substituted; linear and branched, optionally substituted $C_1$-$C_8$ alkyl radicals; and linear and branched, optionally substituted $C_1$-$C_8$ alkoxy radicals;

$R_7$, which may be identical or different, is chosen from a hydrogen atom; linear and branched, optionally substituted $C_1$-$C_4$ alkyl radicals; linear and branched, optionally substituted $C_1$-$C_8$ alkoxy radicals; optionally substituted $C_6$ aryl radicals; amino radicals; amino radicals substituted with at least one substituent, which may be identical or different, chosen from linear and branched $C_1$-$C_8$ and, for example, $C_1$-$C_4$ alkyl radicals, which are optionally substituted, for example, with at least one substituent chosen from a hydroxyl radical, linear and branched $C_1$-$C_4$ alkoxy radicals, linear and branched $C_1$-$C_4$ thioalkyl radicals, linear and branched $C_1$-$C_4$ alkylsulfonamido radicals, optionally substituted $C_6$ aryl radicals, and optionally substituted 5- to 6-membered heteroaryl radicals; a hydroxyl radical; a nitro radical; and a cyano radical; z is equal to 4; and z' is equal to 3.

In addition, the chromophore is linked to the linker via $R_6$ or $R_7$, or via the ring. In this case, the radical borne by the ring represents a single bond between the chromophore and the linker.

As indicated above, the at least one mixed dye disclosed herein may comprise at least one chromophore chosen from methine compounds.

In one embodiment, the methine compounds are chosen from compounds comprising at least one sequence chosen from >C=C< and —N=C<, wherein the two atoms of the at least one sequence are not simultaneously engaged in a ring. It is pointed out, however, that one of the nitrogen or carbon atoms of the sequences may be engaged in a ring.

In one embodiment, the chromophores of the methine family are radicals derived from chromophores of methine, azomethine, mono- and di-arylmethane, indamine (and diphenylamine), indophenol, indoaniline, carbocyanin, azacarbocyanin and isomers thereof, diazacarbocyanin and isomers thereof, tetraazacarbocyanin, and hemicyanin.

For example, among the chromophores of the methine family, mention may be made of the chromophores corresponding to formula (IV) below, and tautomeric forms thereof:

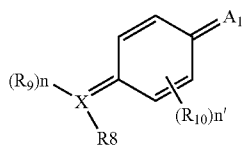

wherein:
- $R_8$ and $R_9$, which may be identical or different, are each chosen from a hydrogen atom; $C_6$-$C_{30}$ aryl radicals, ($C_1$-$C_8$)alkylaryl radicals, wherein the aryl portion is optionally substituted with at least one substituent, which may be identical or different, for example, chosen from a hydroxyl radical, linear and branched, substituted and unsubstituted $C_1$-$C_4$ alkoxy radicals, amino radicals, amino radicals substituted with at least one substituent, which may be identical or different, chosen from linear and branched, $C_1$-$C_4$ alkyl radicals, optionally bearing at least one entity chosen from a hydroxyl radical and halogen atoms, for example, chlorine; and heterocyclic radicals chosen, for example, from thiophene, furan, piperonyl, indole, indoline, pyridine, carbazole, dehydroquinoline and chromone heterocycles;
- $R_8$ and $R_9$ also cannot simultaneously represent either an aromatic radical or a heteroaromatic radical;
- $R_{10}$, which may be identical or different, is chosen from a hydrogen atom; linear and branched, optionally substituted $C_1$-$C_8$ alkyl radicals; optionally substituted $C_6$-$C_{30}$ aryl radicals; amino radicals; amino radicals substituted with at least one substituent chosen from linear and branched $C_1$-$C_4$ alkyl radicals, optionally bearing at least one hydroxyl radical; a hydroxyl radical; linear and branched $C_1$-$C_8$ alkoxy radicals, optionally bearing at least one substituent chosen from a hydroxyl radical and $C_1$-$C_4$ alkoxy radicals; and halogen atoms, for example, chlorine;
- X is chosen from a nitrogen atom and a carbon atom;
- n is equal to 0 when X is a nitrogen atom, and 1 when X is a carbon atom;
- n' is equal to 4; and
- $A_1$ is chosen from amino radicals; amino radicals substituted with at least one substituent, which may be identical or different, chosen from linear and branched $C_1$-$C_8$ alkyl radicals, optionally bearing at least one substituent chosen from a hydroxyl radical and $N^+(R_{11})_2$ ammonium radicals, wherein $R_{11}$, which may be identical or different, is chosen from optionally substituted $C_1$-$C_8$ alkyl radicals; and $C_6$ aryl radicals, which are optionally substituted, for example, with at least one substituent chosen from a hydroxyl radical, halogen atoms, for example, chlorine and fluorine, a nitro radical, a cyano radical, linear and branched $C_1$-$C_4$ alkoxy radicals, linear and branched $C_1$-$C_4$ monohydroxyalkoxy radicals, linear and branched $C_2$-$C_4$ polyhydroxyalkoxy radicals, and amino radicals, which are optionally substituted with at least one substituent, which may be identical or different, chosen from linear and branched $C_1$-$C_4$ alkyl radicals and hydroxyalkyl radicals.

Moreover, the chromophore is linked to the linker via the group $A_1$ or via one of the radicals $R_8$, $R_9$, $R_{10}$ and $R_{11}$ or directly to the (hetero)aromatic ring(s). In the latter case, the radical $R_{10}$ concerned then represents a single bond between the chromophore and the linker.

In one embodiment, when $R_8$ or $R_9$ is chosen from $C_6$ aryl radicals, this radical may optionally be substituted, for example, with at least one substituent, which may be identical or different, chosen from a hydroxyl radical; amino radicals; amino radicals substituted with at least one substituent, which may be identical or different, chosen from linear and branched $C_1$-$C_8$ alkyl radicals, optionally bearing at least one hydroxyl group; halogen atoms; linear and branched $C_1$-$C_{12}$ alkylsulfonamido radicals (alkyl-$SO_2$—NH—); linear and branched $C_1$-$C_{12}$ alkylsulfamoyl radicals (alkyl-NH—$SO_2$—); acyloxy radicals, wherein the linear or branched alkyl portion is chosen from $C_1$-$C_{12}$ alkyl radicals; alkoxycarbonyl radicals wherein the linear or branched alkyl portion is chosen from $C_1$-$C_{12}$ alkyl radicals; and carboxyl radicals.

Chromophores of the methine family that are also suitable are those of formula (V) below and, where appropriate, tautomeric forms thereof:

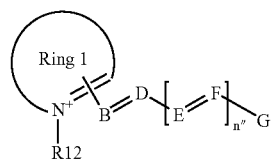

wherein:
- B, D, E and F, which may be identical or different, are each chosen from a nitrogen atom and groups C—$R_{13}$, wherein $R_{13}$, which may be identical or different, is chosen from a hydrogen atom, $C_1$-$C_8$ alkyl radicals which are optionally substituted, for example, with at least one hydroxyl radical; linear and branched $C_1$-$C_4$ alkoxy radicals; amino radicals; amino radicals substituted with at least one substituent, which may be identical or different, chosen from linear and branched $C_1$-$C_4$ alkyl radicals, optionally bearing at least one hydroxyl group; optionally substituted $C_6$ aryl radicals; and optionally substituted 5- to 12-membered heteroaryl radicals;
- n"=0 or 1;
- G represents a Ring 4, or the residues:

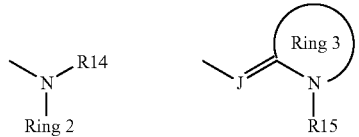

wherein:
- $R_{12}$ and $R_{15}$, which may be identical or different, are each chosen from linear and branched, optionally substituted $C_1$-$C_8$ alkyl radicals and optionally substituted benzyl radicals;
- $R_{14}$ is chosen from a hydrogen atom, $C_1$-$C_8$ alkyl radicals which are optionally substituted, for example, with at least one substituent chosen from a hydroxyl radical, linear and branched $C_1$-$C_4$ alkoxy radicals, amino radicals, amino radicals substituted with at least one substituent, which may be identical or different, chosen from linear and branched $C_1$-$C_4$ alkyl radicals, optionally bearing at least one hydroxyl radical; optionally substituted $C_6$ aryl radicals; and optionally substituted $C_2$-$C_{12}$ heteroaryl radicals;

J is chosen from a nitrogen atom and groups C—$R_{16}$; wherein $R_{16}$ is chosen from a hydrogen atom, $C_1$-$C_8$ alkyl radicals which are optionally substituted, for example, with at least one hydroxyl radical; linear and branched $C_1$-$C_4$ alkoxy radicals; amino radicals; amino radicals substituted with at least one substituent, which may be identical or different, chosen from linear and branched $C_1$-$C_4$ alkyl radicals, optionally bearing at least one hydroxyl group; optionally substituted $C_6$ aryl radicals; and optionally substituted 5- to 12-membered heteroaryl radicals;

Ring 1 is chosen from 5- to 12-membered heteroaromatic radicals, bearing at least one cationic charge on a nitrogen atom and optionally comprising at least one other hetero atom chosen from nitrogen, oxygen and sulfur; wherein the heteroaromatic radicals are optionally substituted with at least one substituent chosen from linear and branched, substituted and unsubstituted $C_1$-$C_8$ alkyl radicals; linear and branched, substituted and unsubstituted $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; $C_5$-$C_6$ aromatic radicals; a hydroxyl radical; linear and branched $C_1$-$C_8$ alkoxycarbonyl radicals; a nitro radical; a cyano radical; linear and branched $C_1$-$C_{12}$ alkylsulfonamido radicals (alkyl-$SO_2$—NH—); and $C_1$-$C_{12}$ linear and branched alkylsulfamoyl radicals (alkyl-NH—$SO_2$—);

Ring 2 is chosen from $C_6$-$C_{12}$ aromatic radicals; 5- to 12-membered heteroaromatic radicals, comprising at least one hetero atom chosen from nitrogen, oxygen and sulfur; wherein the aromatic and heteroaromatic radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; (hetero)aromatic radicals, which may, for example, be a 5- to 6-membered (hetero)aromatic radical; and a hydroxyl radical. In one embodiment, Ring 2 is chosen from $C_6$-$C_{30}$ aromatic radicals, optionally substituted as indicated above;

Ring 3 is chosen from 5- and 6-membered heteroaromatic radicals comprising at least one hetero atom chosen from nitrogen, oxygen and sulfur; wherein the heteroaromatic radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; $C_5$-$C_6$ aromatic radicals; a hydroxyl radical; linear and branched $C_1$-$C_8$ alkoxycarbonyl radicals; a nitro radical; a cyano radical; linear and branched $C_1$-$C_{12}$ alkylsulfonamido radicals (alkyl-$SO_2$—NH—); and linear and branched $C_1$-$C_{12}$ alkylsulfamoyl radicals (alkyl-NH—$SO_2$—); and Ring 4 is chosen from $C_6$-$C_{12}$ aromatic radicals; 5- to 12-membered heteroaromatic radicals, comprising at least one hetero atom chosen from nitrogen, oxygen and sulphur, wherein the aromatic and heteroaromatic radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl group; (hetero)aromatic radicals, for example, 5- and 6-membered (hetero)aromatic radicals; and a hydroxyl radical;

provided that when n" is 1 and G represents a ring, then B, D, E and F cannot simultaneously be a nitrogen atom; and that when n" is 0 and G represents a ring, then B and D are not simultaneously a nitrogen atom.

Moreover, the chromophore is linked to the linker via one of the radicals $R_{12}$, $R_{13}$, $R_{14}$, $R_{15}$ and $R_{16}$ or the rings. In this case, the radical borne by the ring represents a single bond between the chromophore and the linker.

Formula (V) includes the positional isomers corresponding to the various possibilities of insertion of the bond of B onto the ring 1 relative to the quaternized nitrogen atom.

In one embodiment, the chromophores of the methine family are chosen from compounds of the following formulae, and tautomeric forms thereof:

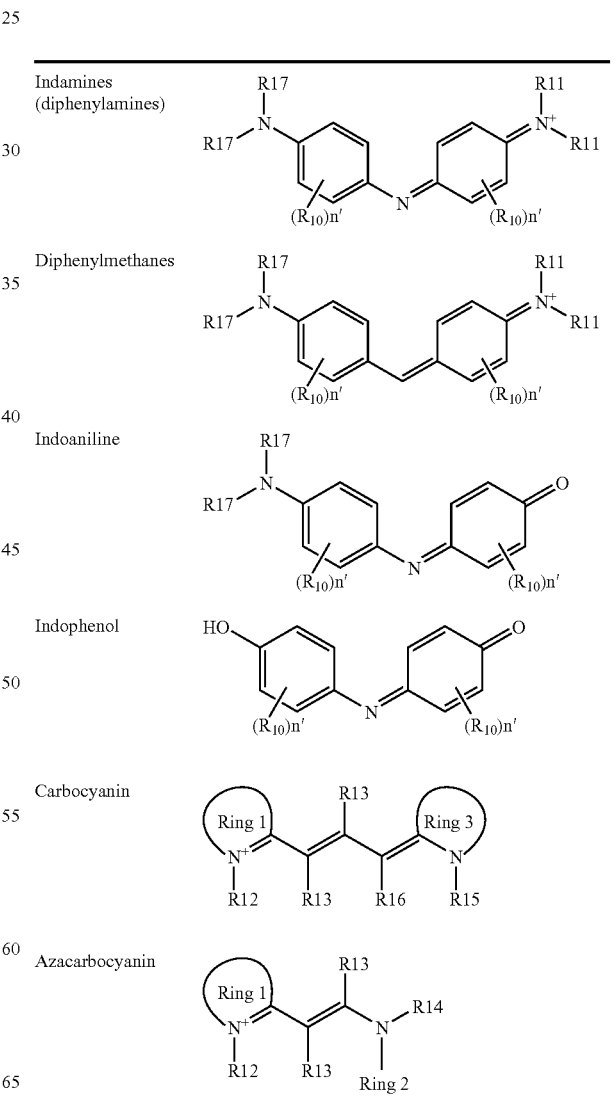

-continued

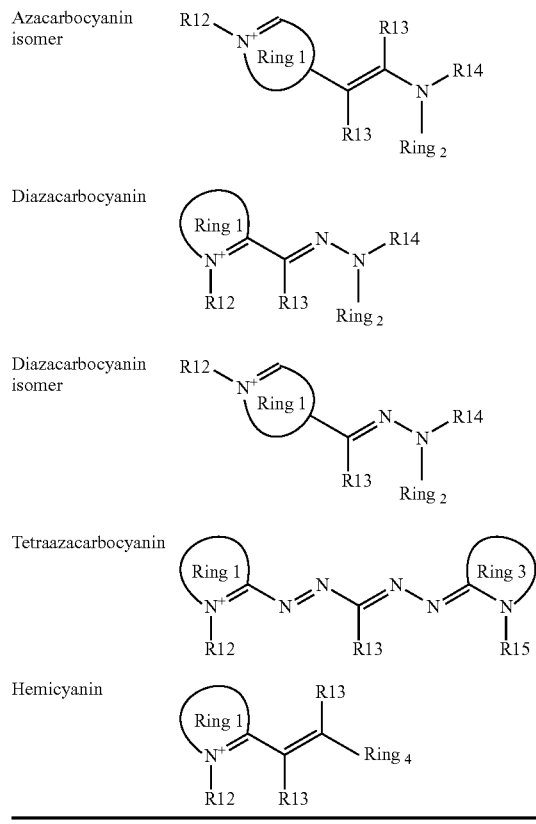

wherein:

$R_{17}$, which may be identical or different, is chosen from a hydrogen atom, optionally substituted $C_1$-$C_8$ alkyl radicals; $C_6$ aryl radicals, which are optionally substituted, for example, with at least one substituent chosen from a hydroxyl radical, halogen atoms, for example, chlorine and fluorine, a nitro radical, a cyano radical, linear and branched $C_1$-$C_4$ alkoxy radicals, linear and branched $C_1$-$C_4$ monohydroxyalkoxy radicals, linear and branched $C_2$-$C_4$ polyhydroxyalkoxy radicals, amino radicals, which may be optionally substituted with at least one substituent, which may be identical or different, chosen from linear and branched $C_1$-$C_4$ alkyl and hydroxyalkyl radicals; and the groups and radicals $R_{11}$, $R_{12}$, $R_{13}$, $R_{14}$, $R_{15}$, $R_{16}$, $Ring_1$, $Ring_2$, $Ring_3$ and $Ring_4$ being defined as above.

In one embodiment, the Ring 1 is chosen from imidazolium, pyridinium and indolinium rings, optionally substituted as indicated previously.

In a further embodiment, Ring 3 is chosen from imidazole, pyridine, and indoline rings, optionally substituted as indicated previously.

In one embodiment, Ring 2 is chosen from $C_6$ aromatic radicals, optionally substituted as indicated previously.

In one embodiment, Ring 4 is chosen from $C_6$ aromatic radicals, optionally substituted as indicated previously.

It should be pointed out that the chromophore may be linked to the linker via one of the groups $R_{10}$, $R_{11}$, $R_{12}$, $R_{13}$, $R_{14}$, $R_{15}$ and $R_{16}$ or via an aromatic or heteroaromatic ring. In the case of attachment via a ring, the radical borne on the ring represents a single bond between the chromophore and the linker.

In one embodiment, the chromophore is chosen from the compounds of formula (V) and, for example, from diazacarbocyanins and isomers thereof, and hemicyanins. In one embodiment, $R_{13}$, which may be identical or different, is chosen from a hydrogen atom, $C_1$-$C_8$ alkyl radicals, which are optionally substituted, for example, with at least one hydroxyl radical; optionally substituted $C_6$ aryl radicals; n=0; G is chosen from Ring 4 and —N($R_{14}$)-Ring 2 wherein $R_{14}$ is chosen from a hydrogen atom, $C_1$-$C_8$ alkyl radicals, which are optionally substituted, for example, with at least one hydroxyl radical; Ring 2 and Ring 4, which may be identical or different, are each chosen from optionally substituted $C_6$ aromatic radicals.

In one embodiment, the chromophore and the linker are linked via the radical $R_{12}$.

It should be noted that the chromophores described above may be prepared according to the teaching of the following patent applications and patents, the disclosures of which relate to such preparations are incorporated herein by reference: GB 822 846; DE 1 254 118; GB 1 047 796; U.S. Pat. Nos. 3,652,556; 3,423,427; BE 702 239; GB 702 240; U.S. Pat. Nos. 3,995,088; 4,054,718; 4,670,385; 5,094,688; and 5,097,034.

The at least one mixed dye may similarly comprise at least one chromophore chosen from carbonyl compounds.

Among the chromophores of this type, examples that may be mentioned include chromophores derived from dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

In one embodiment, the chromophore of the carbonyl family is a radical derived from compounds of formula (VI) below:

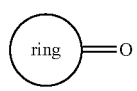

wherein: the ring represents a 5- or 6-membered ring, at least one of the ring members of which is optionally replaced with at least one entity chosen from oxygen, nitrogen and sulphur hetero atoms and additional carbonyl functional groups; wherein the ring is optionally substituted with at least one substituent chosen from optionally substituted linear and branched $C_1$-$C_8$ alkyl radicals; a hydroxyl radical; halogen atoms, for example, chlorine; nitro, cyano, amino and alkylamino radicals; and wherein the ring is optionally fused with at least one $C_6$ aromatic ring, this or these ring(s) themselves possibly being fused with at least one aromatic ring, at least one of the carbon atoms of the at least one aromatic ring is optionally replaced with at least one hetero atom chosen from oxygen, nitrogen and sulfur.

Moreover, the chromophore is linked to the linker via one of the radicals substituting the rings or via a ring. In the latter case, the radical borne by the ring represents a single bond between the chromophore and the linker.

In one embodiment, the chromophore of the carbonyl family is chosen from compounds of the following formulae, and tautomeric forms thereof:

Acridones
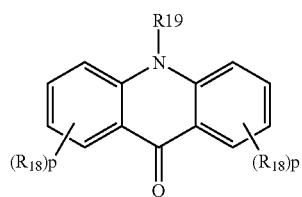
Anthraquinones
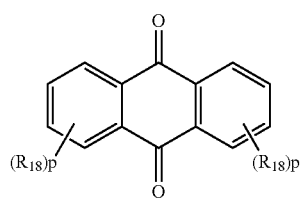
Benzanthrones
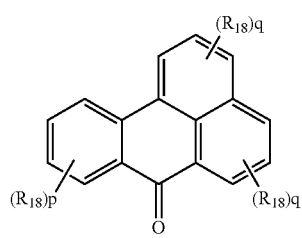
Benzoquinones
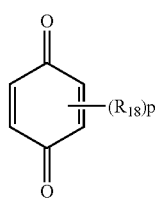
Flavones
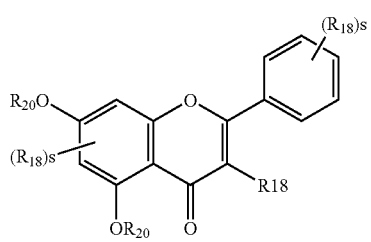
Indanthrones
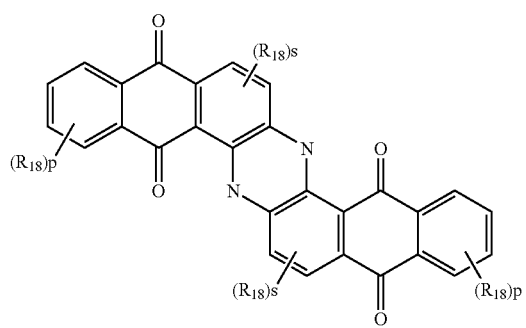

-continued

Naphthoquinones

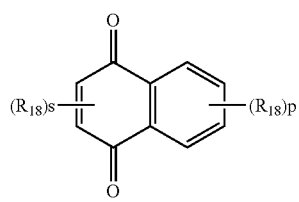

Quinacridones

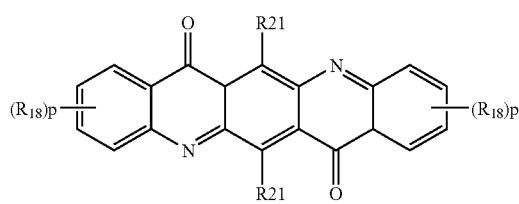

Indigoids

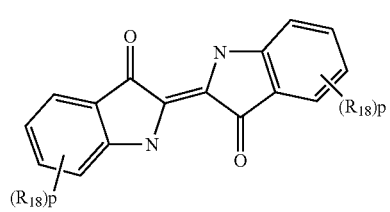

Thioindigos

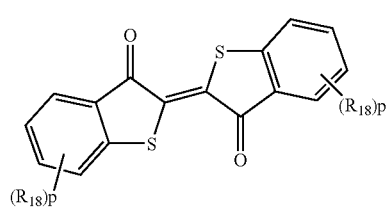

Naphthalimides

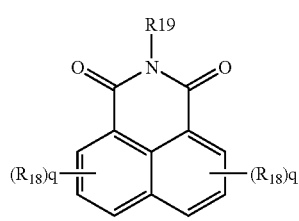

Diketopyrrolopyrroles

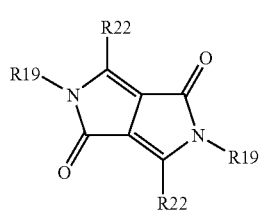

Coumarins

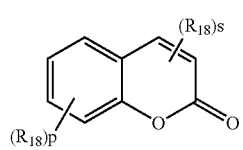

wherein:

$R_{18}$, $R_{19}$, $R_{21}$, which may be identical or different, are each chosen from a hydrogen atom; linear and branched, optionally substituted $C_1$-$C_8$ alkyl radicals; a hydroxyl radical; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl group; halogen atoms and, for example, chlorine and fluorine; a nitro radical; and a cyano radical;

$R_{20}$ is chosen from a hydrogen atom and linear and branched, optionally substituted $C_1$-$C_8$ alkyl radicals; $R_{22}$, which may be identical or different, is chosen from $C_6$ aryl radicals, which is optionally substituted, for example, with at least one substituent chosen from a hydroxyl radical, amino radicals, amino radicals substituted with at least one substituent, which may be identical or different, chosen from linear and branched $C_1$-$C_8$ alkyl radicals, optionally bearing at least one hydroxyl radical; linear and branched $C_1$-$C_8$ alkoxy radicals optionally bearing at least one hydroxyl radical; halogen atoms, for example, chlorine and fluorine; a nitro radical; and a cyano radical;

p is equal to 4; q is equal to 3; r is equal to 5; and s is equal to 2.

The chromophore may be linked to the linker via one of the radicals $R_{18}$, $R_{19}$, $R_{20}$, $R_{21}$ or $R_{22}$ or via one of the aromatic or heteroaromatic rings. In this case, the radical borne by the ring represents a single bond between the chromophore and the linker.

Thus, as examples of the at least one mixed dye comprising two chromophores mention may be made of the following:
azine-linker-azine,
azine-linker-methine,
azine-linker-carbonyl,
azine-linker-nitro,
nitro-linker-nitro,
nitro-linker-methine, and
nitro-linker-carbonyl.

As mentioned previously, the chromophores of the at least one mixed dye are linked together by means of at least one linker that stops delocalization of the electrons of each of the chromophores.

Thus, the at least one linker comprises an atom or a group of atoms that isolate(s) each of the chromophores of the at least one mixed dye.

In one embodiment, the bond between the radical and the at least one linker is made by means of a nitrogen or oxygen atom.

It should also be noted that the at least one linker may be cationic or non-cationic.

Furthermore, the at least one linker may be divalent, trivalent or tetravalent.

According to one embodiment, the at least one linker is chosen from linear and branched $C_1$-$C_{20}$ hydrocarbon-base chains, for example, $C_1$-$C_{12}$ hydrocarbon-based chains, such as an alkyl chain, at least one of the carbon atoms of the hydrocarbon-based chains possibly being replaced with at least one entity chosen from hetero atoms such as sulfur, nitrogen, and oxygen, provided that the chain does not comprise two adjacent hetero atoms; saturated and unsaturated 5- and 6-membered heterocycles, for example, comprising at least two nitrogen atoms, wherein the hydrocarbon-based chains are possibly unsaturated or comprise at least one arylene radical; arylene radicals; divalent terephthalamide radicals; and from divalent and trivalent radicals, for example, triazine radicals.

In one embodiment, the at least one linker is chosen from linear and branched $C_1$-$C_{20}$ alkyl chains and, for example, $C_1$-$C_{12}$ alkyl chains, at least one of the carbon atoms of which may be replaced with a saturated or unsaturated 5- or 6-membered heterocycle, for example, comprising at least two nitrogen atoms.

The at least one mixed dye may be prepared according to chemical reactions that are known per se, starting with functionalized chromophores capable of reacting with the chosen linker.

For example, when the at least one linker is a triazine group, then the chromophore comprises a reactive amino, OH or SH group, and the synthesis is performed, for example, according to the schemes below:

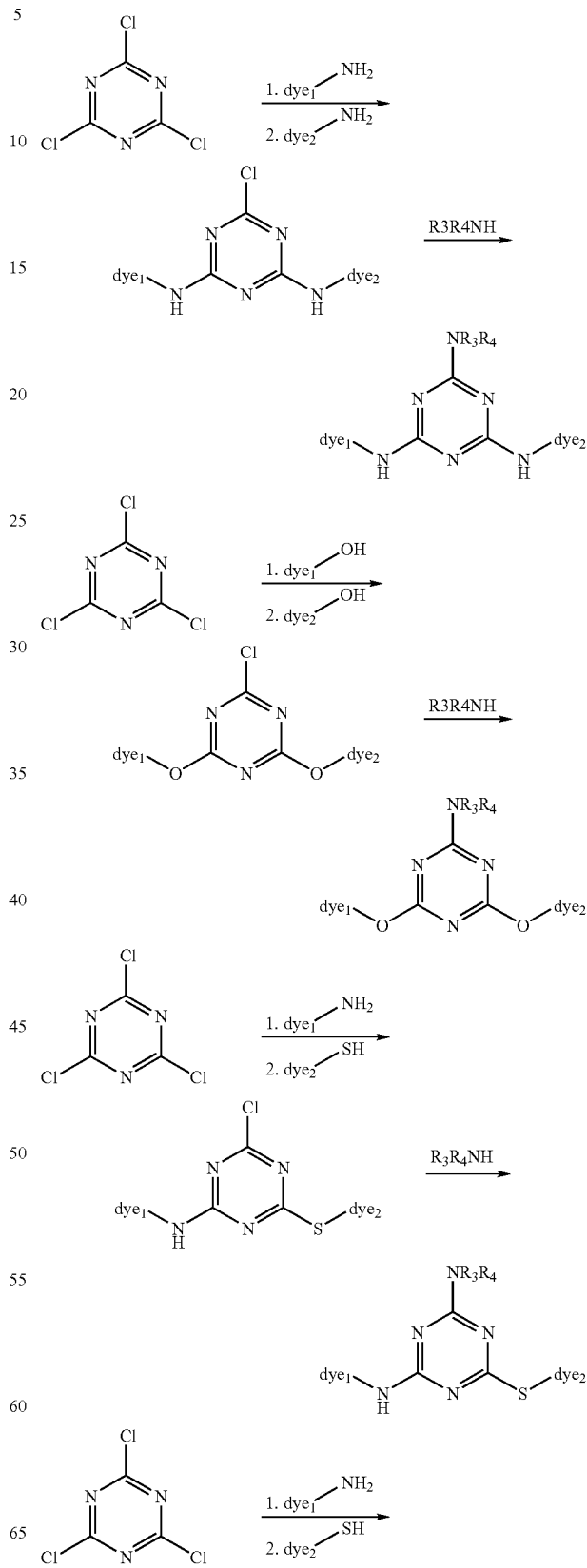

-continued

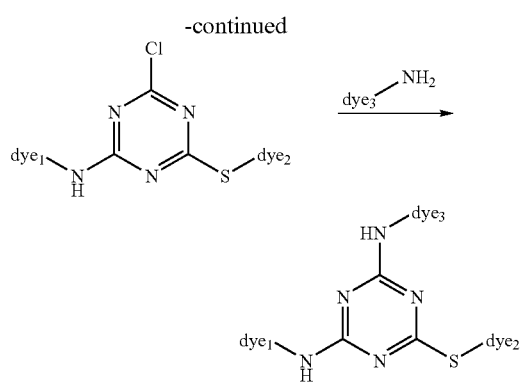

According to a first step, a first chromophore is mixed with the compound capable of forming the at least one linker, for example, trichlorotriazine. When this reaction is complete, a second chromophore is added to the reaction medium. This sequence may be repeated as many times as there are reactive groups on the compound capable of forming the at least one linker.

For the preparation of a mixed dye Dye1-linker-Dye2, the molar ratio of the at least one linker relative to Dye1 ranges, for example, from 10:1 to 0.5:1 and, for example, may be equal to 1:1. This ratio may be modified when more than one linker or several chromophores are used.

The reaction temperature can range from −100° C. to +130° C. and, for example, from −5° C. to 100° C. The reaction time depends on the reactivity of the species present and on the reaction temperature. In general, the reaction time ranges from 10 minutes to 8 hours and, for example, from 30 minutes to 4 hours.

In one embodiment, the pH of the reaction mixture ranges from 2 to 12.

The reaction may also be performed in water and/or in at least one organic solvent.

Several publications describe the reaction for the chemical combination between two identical chromophores. Examples that may be mentioned include the documents ISBN 0901956759, WO 02/78596, DE 198 45 640 and U.S. Pat. No. 5,708,151, the disclosures of which are incorporated herein by reference.

In addition, the reactions or the reactions of a linker with two different compounds, which may or may not be dyes, have been described in the literature, for example in WO 03/029359, DE 3 335 956, WO 03/30909, WO 03/18021, Journal of Medicinal Chemistry 43(9), 2000,1892-97; and Chemiker Zeitung 117(7-8), 1987, 241-5.

According to another possibility, the at least one mixed dye may be obtained according to the following reaction scheme:

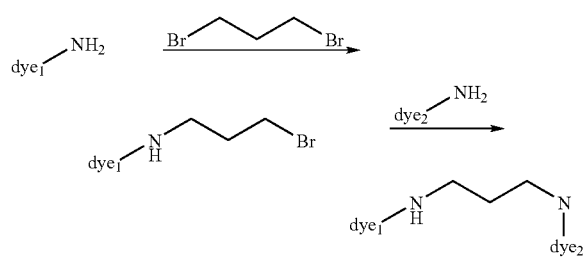

According to a first step, a first chromophore is mixed with the compound capable of forming the at least one linker, for example dibromopropane. When this reaction is complete, a second chromophore is added to the reaction medium. This sequence may be repeated as many times as there are reactive groups on the compound capable of forming the at least one linker.

For the preparation of a mixed dye Dye1-linker-Dye2, the molar ratio of the linker relative to Dye1 ranges from 10:1 to 0.1:1 and, for example, may be equal to 0.5:1. This ratio may be modified when more than one linker or several chromophores are used.

The reaction temperature is may range from −100° C. to +30° C. and, for example, from −5° C. to 100° C. The reaction time depends on the reactivity of the species present and on the reaction temperature. In general, the reaction time ranges from 10 minutes to 24 hours and, for example, from 30 minutes to 4 hours.

The reaction may be performed in water and/or in at least one organic solvent.

In one embodiment, the pH of the reaction mixture ranges from 2 and 12.

The at least one mixed dye may be present in the dye composition in an amount ranging from 0.001% to 20% by weight, for example, from 0.005% to 10% by weight and, further, for example, from 0.01% to 5% by weight, relative to the total weight of the composition.

The dye composition disclosed herein may further comprise at least one additional direct dye other than the at least one mixed dye described herein.

The at least one additional direct dye may be chosen from direct dyes that are conventionally used in the field of dyeing keratin fibers, and, for example, human keratin fibers.

For example, the at least one additional direct dye may be chosen from nitrobenzene dyes, azo additional direct dyes and methine direct dyes. The at least one additional direct dye may be chosen from nonionic, anionic and cationic direct dyes. In one embodiment, the at least one additional direct dye is chosen from cationic direct dyes.

The at least one additional direct dye may be present in the dye composition disclosed herein in an amount ranging from 0.001% to 10% by weight, relative to the total weight of the dye composition.

The dye composition disclosed herein may also comprise at least one oxidation base and/or at least one coupler conventionally used for dyeing keratin fibers, for example, human keratin fibers, such as hair.

The at least one oxidation base may be chosen from para-phenylenediamines, bis(phenyl)alkylenediamines, para-aminophenols, bis-para-aminophenols, ortho-aminophenols, heterocyclic bases, and addition salts thereof.

The at least one oxidation base may be present in the dye composition disclosed herein in an amount ranging from 0.001% to 10% by weight and, for example, from 0.005% to 6% by weight, relative to the total weight of the dye composition.

The at least one coupler may be chosen, for example, from meta-phenylenediamines, meta-aminophenols, meta-diphenols, naphthalene-based couplers, heterocyclic couplers, and addition salts thereof.

In the composition disclosed herein, the at least one coupler may be present in an amount ranging from 0.001% to 10% by weight and, for example, from 0.005% to 6% by weight, relative to the total weight of the dye composition.

In one embodiment, the addition salts, for example, of the oxidation bases and of the couplers that may be used in the dye composition disclosed herein are chosen, for example, from addition salts with an acid, such as hydrochlorides, hydrobromides, sulfates, citrates, succinates, tartrates, lactates, tosylates, benzenesulfonates, phosphates and acetates, and addition salts with a base, such as sodium hydroxide, potassium hydroxide, ammonia, amines and alkanolamines.

The medium that is suitable for dyeing, also known as the dye support, is a cosmetic medium that may be chosen from water and mixtures of water and at least one organic solvent to dissolve the compounds that would not be sufficiently soluble in water.

Examples of the at least one organic solvent include linear and branched and, for example, saturated monoalcohols comprising from 2 to 10 carbon atoms, such as ethanol and isopropanol; aromatic alcohols, such as benzyl alcohol and phenylethyl alcohol; polyols and polyol ethers, for example, ethylene glycol monomethyl, monoethyl and monobutyl ether, propylene glycol and ethers thereof, for example, propylene glycol monomethyl ether, butylene glycol, dipropylene glycol, hexylene glycol (2-methyl-2,4-pentanediol), neopentyl glycol and 3-methyl-1,5-pentanediol; and also diethylene glycol alkyl ethers, for example, $C_1$-$C_4$ alkyl ethers, such as diethylene glycol monoethyl ether and monobutyl ether.

The at least one organic solvent may, for example, be present in an amount ranging from 1% to 40% by weight, relative to the total weight of the dye composition, and further, for example, from 5% to 30% by weight, relative to the total weight of the dye composition.

The dye composition disclosed herein may also comprise at least one adjuvant chosen from various adjuvants conventionally used in compositions for dyeing keratin fibers, for example, human keratin fibers, such as hair. For example, the at least one adjuvant may be chosen from anionic, cationic, nonionic, amphoteric, and zwitterionic surfactants; anionic, cationic, nonionic, amphoteric, and zwitterionic polymers; mineral and organic thickeners, and, for example, anionic, cationic, nonionic and amphoteric associative polymeric thickeners; antioxidants; penetrating agents; sequestering agents; fragrances; buffers; dispersants; conditioning agents, for example, volatile and non-volatile, modified and unmodified silicones; film-forming agents; ceramides, pseudoceramides; preserving agents; and opacifiers.

The at least one adjuvant may be present in an amount ranging from 0.01% to 20% by weight, relative to the total weight of the dye composition.

The dye composition disclosed herein may further comprise at least one oxidizing agent.

The at least one oxidizing agent may be chosen from oxidizing agents conventionally used for the oxidation dyeing of keratin fibers, for example, human keratin fibers. The at least one oxidizing agent may, for example, be chosen from hydrogen peroxide; urea peroxide; alkali metal bromates and ferricyanides; persalts such as perborates and persulfates of alkali metals and of alkaline-earth metals, such as sodium, potassium and magnesium; and peracids and oxidase enzymes, among which mention may be made of peroxidases, two-electron oxidoreductases, such as uricases, and four-electron oxygenases, such as laccases. In one embodiment, hydrogen peroxide may be used.

The composition disclosed herein may further comprise at least one alkaline agent, which may be chosen from those conventionally used in cosmetics.

The at least one alkaline agent may be chosen from aqueous ammonia; alkaline carbonates; alkanolamines, such as monoethanolamine, diethanolamine and triethanolamine,
and derivatives thereof; sodium hydroxide; potassium hydroxide and compounds of formula (A) below:

wherein: W is a propylene residue optionally substituted with at least one substituent chosen from hydroxyl radicals and $C_1$-$C_4$ alkyl radicals; $R_a$, $R_b$, $R_c$ and $R_d$, which may be identical or different, are each chosen from a hydrogen atom, $C_1$-$C_4$ alkyl and $C_1$-$C_4$ hydroxyalkyl radicals.

The pH of the dye composition disclosed herein may, for example, range from 8 to 11.

Needless to say, a person skilled in the art will take care to select this or these optional additional compound(s) such that the advantageous properties intrinsically associated with the composition disclosed herein are not, or are not substantially, adversely affected by the envisaged addition(s).

The dye composition disclosed herein may be in various forms, for example, in a form chosen from liquids, creams and gels, and any other forms that are suitable for dyeing keratin fibers, for example, human keratin fibers, such as hair.

The process disclosed herein is a process that comprises applying at least one dye composition, as defined above, to wet or dry fibers.

According to one embodiment, the at least one dye composition applied to the keratin fibers does not comprise any oxidizing agent. This embodiment is particularly suitable when the at least one dye composition comprises the at least one mixed dye and optionally at least one additional direct dye.

According to another embodiment, the process is performed with at least one oxidizing agent. This embodiment is suitable irrespective of the nature of the dyes present (mixed dye, additional direct dye, oxidation bases and/or couplers). This process also allows lightening of the treated fiber to be obtained.

According to this embodiment, the at least one oxidizing agent may be added to the at least one dye composition at the time of use, or it may be used starting with at least one oxidizing composition comprising it, which is applied simultaneously with or sequentially to the at least one dye composition comprising the at least one mixed dye. In this latter case, the at least one oxidizing agent is present in a composition different from the one comprising the at least one mixed dye.

According to one embodiment, the at least one dye composition comprising the at least one mixed dye is mixed, for example, at the time of use, with at least one oxidizing composition comprising, in a medium that is suitable for dyeing, at least one oxidizing agent, the at least one oxidizing agent being present in an amount that is sufficient to obtain the desired lightening.

The mixture obtained is then applied to the keratin fibers.

After an action time that is sufficient to obtain the desired coloration, for example, ranging from 3 to 50 minutes and, further, for example, from 5 to 30 minutes, the keratin fibers may, for example, be rinsed, and then washed with shampoo, rinsed again and then dried or left to dry.

Moreover, the at least one dye composition may be conventionally left to act at a temperature ranging from 15 to 80° C. and, for example, from 15 to 40° C.

The at least one oxidizing composition may also comprise at least one adjuvant chosen from various adjuvants conventionally used in compositions for dyeing keratin fibers, for example, human keratin fibers, and as defined above.

The pH of the at least one oxidizing composition comprising the at least one oxidizing agent is such that, after mixing with the at least one dye composition, the pH of the resulting composition applied to the keratin fibers (i.e. in other words the ready-to-use composition), for example, ranges from 7 to 12 and, further, for example, from 8 to 11. It may be adjusted to the desired value by means of at least one agent chosen from acidifying and basifying agents.

Among the acidifying agents, examples that may be mentioned include mineral and organic acids, for example, hydrochloric acid, orthophosphoric acid, sulfuric acid, and acetic acid.

As regards the basifying compounds, reference may be made to the list given hereinabove.

The ready-to-use composition, i.e. in other words the composition that is finally applied to the keratin fibers, may be in various forms, such as in the form chosen from liquids, creams and gels, and in any other forms that are suitable for dyeing keratin fibers, for example, human keratin fibers, such as hair.

Further disclosed herein is a multi-compartment device in which at least one first compartment comprises at least one dye composition comprising at least one mixed dye as described previously, and optionally at least one additional direct dye different from the at least one mixed dye, optionally at least one oxidation base, optionally at least one coupler, and another compartment comprising at least one oxidizing agent.

It should be noted that the at least one mixed dye, optionally the at least one additional direct dye, the at least one oxidation base and the at least one coupler may be in the same compartment or in several compartments; the same compartment possibly comprising only one type of dye (mixed dye, additional direct dye or oxidation dye) or a combination of several of these dyes.

This device may be equipped with a means for applying the desired mixture to the fibers to be treated, such as the devices described in Patent No. FR 2 586 913.

Further disclosed herein are mixed dyes per se, and addition salts thereof, as have just been described, with the exception of mixed dyes having two chromophores one of which is a benzene nitro compound and the other an anthraquinone or benzene nitro compound; wherein the two chromophores are connected by a nitrogen atom through a linker comprising an alkyl radical optionally interrupted by a nitrogen atom carrying one or two radicals chosen from hydrogen, $C_1$-$C_4$ alkyl radicals and $C_1$-$C_4$ hydroxyalkyl radicals. In one embodiment, the mixed dye is not a mixed dye having two chromophores one of which is a benzene nitro compound and the other an anthraquinone or benzene nitro compound; wherein the two chromophores are connected via a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals and, further, the mixed dye is not one of the following compounds:

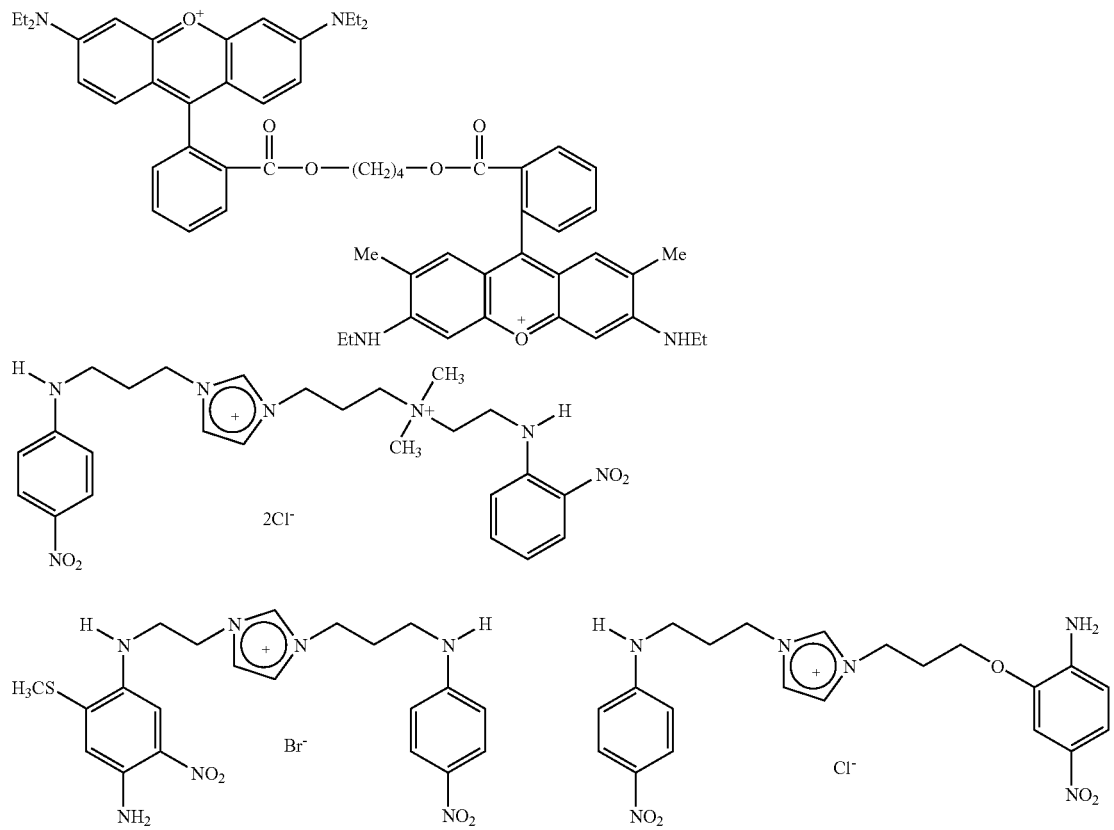

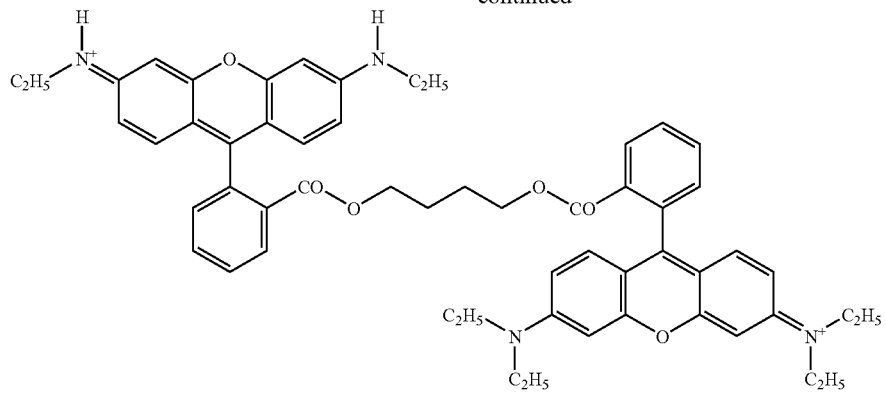

It is also specified that the dyeing composition, in one embodiment disclosed herein does not comprise the above compounds.

For example, the at least one mixed dye disclosed herein does not correspond to a dichromophore comprising two benzene nitro compounds, or to a benzene nitro compound and to an anthraquinone compound.

The at least one mixed dye may be, for example, the following compound, and addition salts thereof:

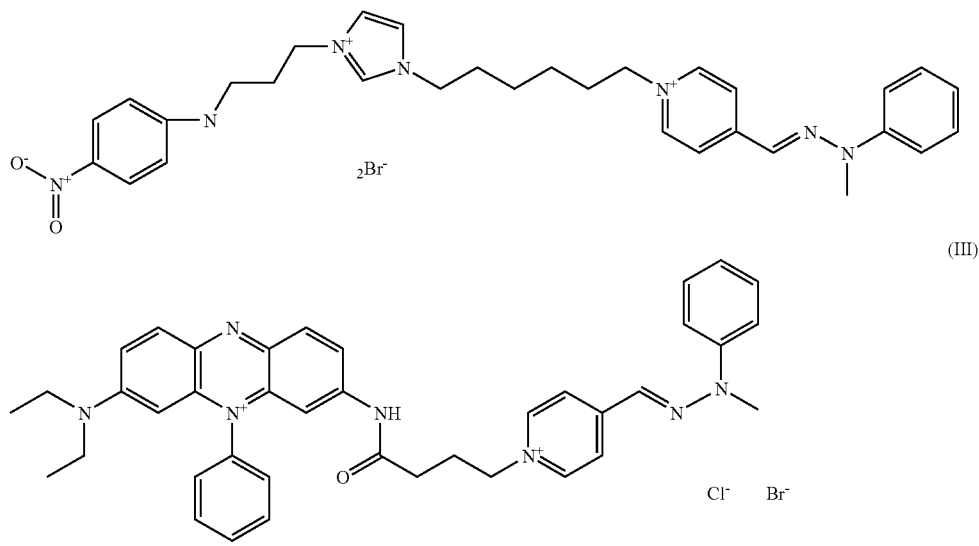

Non-limiting examples of the present disclosure will now be given.

EXAMPLE 1

Synthesis of the Mixed Dye

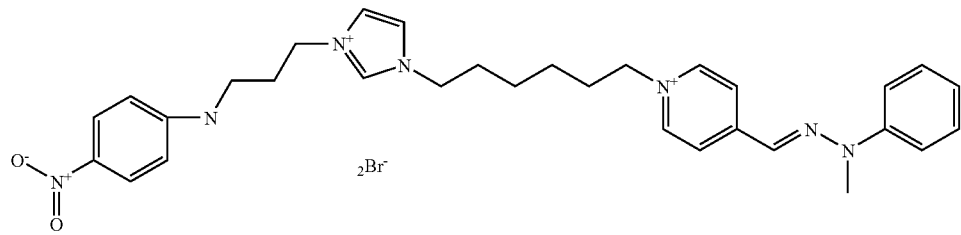

Reaction Scheme:

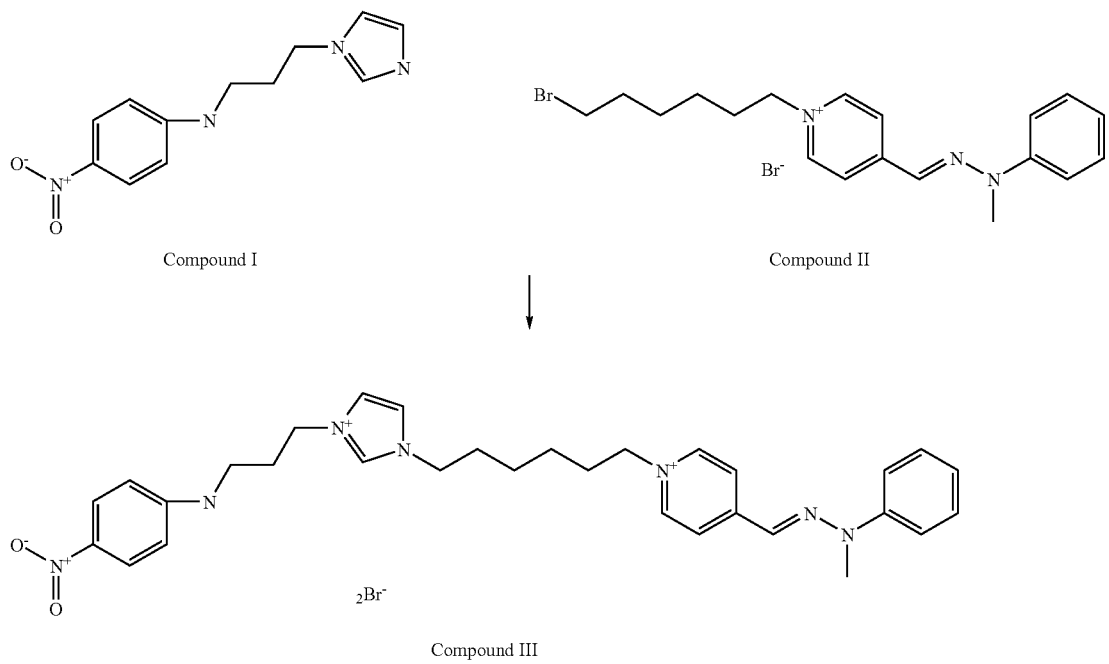

Compounds I (3.33 g) and II (6.16 g) were mixed in dimethylformamide (DMF) (100 ml) and stirred at 90° C. for 18 hours.

The mixture was poured onto ethyl acetate (300 ml), giving a gum.

The gum was taken up in methanol (100 ml), filtered and evaporated to dryness. This gave flakes (6.0 g).

The NMR and mass spectra were in accordance with the structure of the expected product.

DYEING EXAMPLES

1—Dyeing Composition

The mixed dye obtained in the previous example was formulated at $5.7 \times 10^{-4}$ mol % in the dye composition A.

| Composition A | |
| --- | --- |
| (50/50 $C_8/C_{10}$) alkyl polyglucoside as a buffered aqueous 60% solution | 10 g |
| Benzyl alcohol | 10 g |
| Polyethylene glycol 400 containing 8 ethylene oxide units | 12 g |
| Mixed dye from Example 1 | $5.7 \times 10^{-4}$ mol |
| 20.5% aqueous ammonia | 10 g |
| Demineralized water | qs 100 g |

At the time of use, composition A was mixed with 20 volumes aqueous hydrogen peroxide solution (weight for weight, pH=3.5).

The pH of the dye composition after mixing ranged from 9.5 to 10.

The mixture was then applied to locks of heavily bleached natural grey hair containing 90% white hairs (alkaline solubility (AS)=83%).

The action time on the locks was 20 min. at room temperature.

Dyed locks were obtained.

2/Shampoo-fastness

Locks of natural hair containing 90% white hairs and strongly bleached (alkaline solubility (AS)=83%) were dyed with the dye composition disclosed herein (see the preceding paragraph) and with a comparative composition comprising an equimolar mixture of the dyes I and II which constitute the mixed dye:

Yellow Nitro Dye (I):

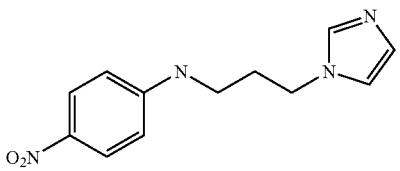

Yellow Hydrazone Dye (II):

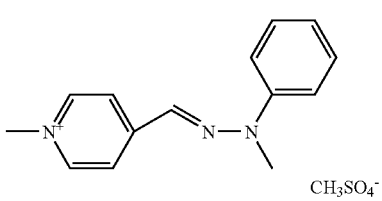

The dyed locks were shampooed six times, with intermediate drying between two shampoo washes.

The color after the six shampoo washes was compared with the initial color of the dyed lock, visually and by calorimetric measurement (Minolta CM2002 calorimeter, illuminant D65-10° CSI).

The shampoo fastness was measured according to the ΔE formula below, using the L*a*b* values measured before ($L_0^*a_0^*b_0^*$) and after ($L_1^*a_1^*b_1^*$) the 6 shampoo washes.

$$\Delta E = \sqrt{(L_1^* - L_0^*)^2 + (a_1^* - a_0^*)^2 + (b_1^* - b_0^*)^2}$$

Thus, the lower the value of ΔE, the better the fastness to repeated shampooings.

The calorimetric results were collated in Tables 1 and 2.

TABLE 2

| Type of hair | L* | a* | b* | Degradation(ΔE) |
|---|---|---|---|---|
| Composition according to the present disclosure: | | | | |
| Mixed dye before shampooing | 63.81 | 7.04 | 73.39 | 3.23 |
| Mixed dye after shampooing | 65.78 | 4.50 | 73.07 | |
| Comparative compositions: | | | | |
| Mixture of dyes I and II before shampooing | 65.45 | 1.88 | 70.41 | 19.29 |
| Mixture of dyes I and II after shampooing | 68.85 | -2.47 | 51.93 | |

These tables indicate that the mixed dye was substantially more fast to repeated shampooings than was the physical mixture of the two dyes.

EXAMPLE 2

Synthesis of the Mixed Dye

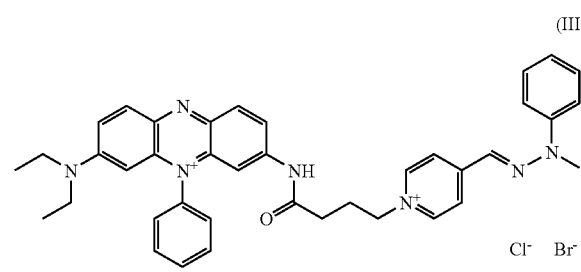

(III)

Reaction Scheme:

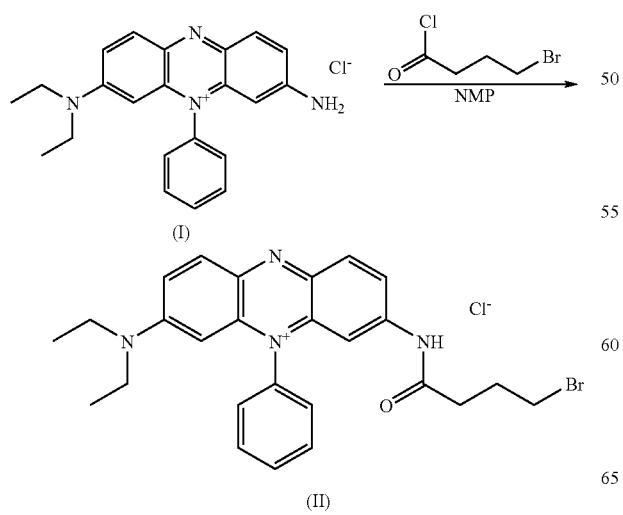

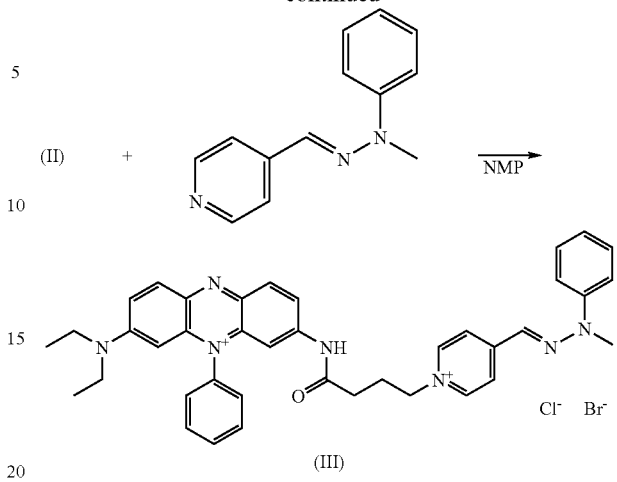

Procedure:

First Stage of Synthesis:

In a 100 mL round-bottom flask, 2 g of pure Basic Violet 5 (compound (I)) was dissolved in 15 mL of N-methylpyrrolidone (NMP), the mixture remained was shaken at room temperature for one hour. 2 mL of 4-bromobutyroyl was introduced in the mixture drop by drop for three minutes.

The reaction mixture was shaken at room temperature for 16 hours and was then poured into 200 mL acetone.

The purple-black precipitate (compound (II)) thus procured was filtered, washed with acetone, and then dried in a vacuum environment.

2.9 of purple powder was collected.

Second Stage of Synthesis:

In a 100 mL round-bottom flask, 2 g of compound (II) procured earlier was mixed in 2 g of isonicotinaldehyde methyl(phenyl)hydrazone and 10 mL of NMP.

The mixture was brought to 80° C. for 24 hours.

It was then poured into 200 mL of acetone.

A purple precipitate formed. It was dried in a vacuum environment. The resulting product was consistent with compound (III) (80% purity according to LC-MS). Compound (III) was produced pure by successive washings in an aqueous solution of raw product with 1-butanol, and then this solution was concentrated in a vacuum environment.

Example of Dyeing

With an aqueous solution of compound (III) (40 mg in 100 mL water), locks of grey hair were dyed a brown shade that was very aesthetic and shampoo resistant.

What is claimed is:

1. A dye composition comprising, in a medium that is suitable for dyeing keratin fibers, at least one mixed dye comprising at least two chromophores, wherein at least one of the chromophores is chosen from cyclic azine and (hetero)aromatic nitro compounds, optionally associated with at least one chromophore chosen from methine and carbonyl compounds, wherein the at least two chromophores are linked together via at least one linker that stops delocalization of the electrons of each of the chromophores;

with the following exceptions:
the dye composition is not a composition comprising a mixed dye comprising two chromophores, one of which is a benzene nitro compound and the other an anthraquinone or benzene nitro compound; wherein the two chromophores are connected by a nitrogen atom through a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals, and the dye composition does not comprise compounds of the following formulae:

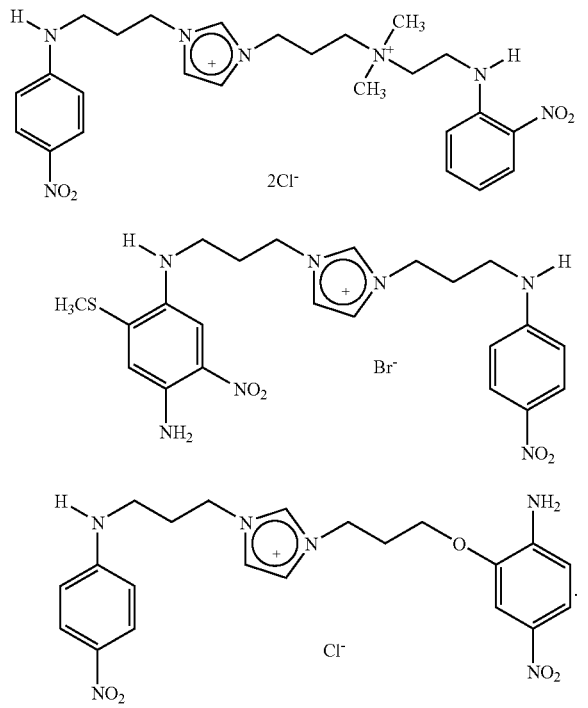

2. The composition according to claim 1, wherein the keratin fibers are human keratin fibers.

3. The composition according to claim 1, wherein the at least one mixed dye comprises at least two different chromophores, at least one of which bears at least one cationic charge.

4. The composition according to claim 3, wherein the at least two different chromophores absorb in the visible range from 400 to 800 nm.

5. The composition according to claim 1, wherein the at least one mixed dye comprises two to four chromophores.

6. The composition according to claim 5, wherein the at least one mixed dye comprises two to three chromophores.

7. The composition according to claim 1, wherein the at least one mixed dye comprises two chromophores.

8. The composition according to claim 1, wherein at least one of the chromophores is chosen from cationic chromophores comprising at least one quaternized nitrogen atom.

9. The composition according to claim 1, wherein the at least one mixed dye comprises at least one chromophore chosen from cyclic azine compounds.

10. The composition according to claim 9, wherein the cyclic azine compounds are chosen from azine, xanthene, thioxanthene, fluorindine, acridine, (di)oxazine, (di)thiazine, and pyronine.

11. The composition according to claim 10, wherein the cyclic azine compounds are radicals derived from compounds of formula (I) below and tautomeric forms thereof:

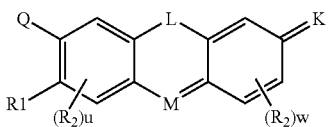

wherein:

L is chosen from hetero atoms, NH, and N—$R_3$;

M is chosen from hetero atoms, $N^+$-$R_3$, CH, and C—$R_4$;

Q and K, which may be identical or different, are each chosen from hydroxyl radicals; amino radicals; amino radicals substituted with at least one substituent, which may be identical or different, chosen from linear and branched $C_1$-$C_8$ alkyl radicals, optionally bearing at least one substituent chosen from hydroxyl radicals, optionally substituted aryl radicals, and optionally substituted ($C_1$-$C_8$)alkylaryl radicals; $N^+(R_5)_t$ ammonium radicals, wherein t is equal to 2 for K and to 3 for Q, $R_5$, which may be identical or different, is chosen from a hydrogen atom; linear and branched $C_1$-$C_8$ alkyl radicals, optionally bearing at least one hydroxyl group; optionally substituted aryl radicals; ($C_1$-$C_8$) alkylaryl radicals, wherein the aryl portion is optionally substituted; optionally substituted linear and branched $C_1$-$C_8$ alkyl radicals; and optionally substituted linear and branched $C_1$-$C_8$ alkoxy radicals; provided that Q and K do not simultaneously represent a $N^+(R_5)_t$ ammonium radical;

$R_1$ and $R_2$, which may be identical or different, are each chosen from a hydrogen atom; optionally substituted linear and branched $C_1$-$C_8$ alkyl radicals; amino radicals; amino radicals optionally substituted with at least one substituent, which may be identical or different, chosen from linear and branched optionally substituted $C_1$-$C_8$ alkyl radicals; optionally substituted phenyl radicals; and halogen atoms, provided that when Q is a substituted or unsubstituted amino radical, or a hydroxyl group, $R_1$ is chosen from alkylamino and alkoxy radicals forming, with the nitrogen or oxygen atom of the radical Q, a 6-membered ring, optionally fused with an aromatic radical, wherein the aromatic radical is optionally substituted with at least one substituent chosen from amino radicals and amino radicals optionally substituted with at least one substituent, which may be identical or different, chosen from optionally substituted linear and branched $C_1$-$C_8$ alkyl radicals and optionally substituted phenyl radicals;

$R_3$ and $R_4$, which may be identical or different, are each chosen from linear and branched $C_1$-$C_8$ alkyl radicals, which are optionally substituted; or $R_3$ and $R_4$, which may be identical or different, are chosen from aryl radicals, which are optionally substituted;

u is equal to 2; and w is equal to 3.

12. The composition according to claim 1, wherein the (hetero)aromatic nitro compounds are chosen from radicals derived from compounds corresponding to formulae (II) and (III) below and tautomeric forms thereof:

Benzene-based

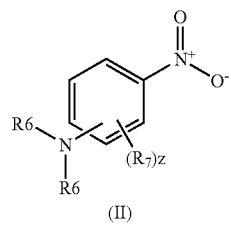
(II)

Pyridine-based

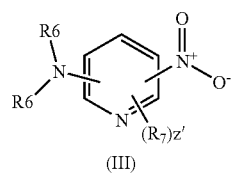
(III)

wherein:

R$_6$, which may be identical or different, is chosen from a hydrogen atom; linear and branched C$_1$-C$_8$ alkyl radicals, optionally bearing at least one hydroxyl group; optionally substituted aryl radicals, (C$_1$-C$_8$)alkylaryl radicals, wherein the aryl portion is optionally substituted; linear and branched, optionally substituted C$_1$-C$_8$ alkyl radicals; and linear and branched, optionally substituted C$_1$-C$_8$ alkoxy radicals;

R$_7$, which may be identical or different, is chosen from a hydrogen atom; linear and branched, optionally substituted C$_1$-C$_4$ alkyl radicals; linear and branched, optionally substituted C$_1$-C$_8$ alkoxy radicals; optionally substituted C$_6$ aryl radicals; amino radicals; amino radicals substituted with at least one substituent, which may be identical or different, chosen from linear and branched C$_1$-C$_8$ radicals; hydroxyl radicals; nitro radicals; and cyano radicals;

z is equal to 4; and z' is equal to 3.

13. The composition according to claim 1, wherein the methine compounds are chosen from compounds comprising at least one sequence chosen from >C=C< and —N=C<, wherein the two atoms of the at least one sequence are not simultaneously engaged in a ring, provided that it is not excluded that one of the nitrogen or carbon atoms of the sequences may be engaged in a ring.

14. The composition according to claim 1, wherein the methine compounds are radicals derived from methine; azomethine; mono- and diarylmethane; indamine; indophenol; indoaniline; carbocyanin; azacarbocyanin and isomers thereof; diazacarbocyanin and isomers thereof; tetraazacarbocyanin; and hemicyanin, and, where appropriate, isomers thereof.

15. The composition according to claim 1, wherein the methine compounds are radicals derived from the following:

(1) chromophores of formula (IV) below and tautomeric forms thereof:

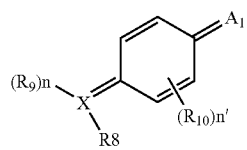
(IV)

wherein:

R$_8$ and R$_9$, which may be identical or different, are each chosen from a hydrogen atom; C$_6$-C$_{30}$ aryl radicals; (C$_1$-C$_8$)alkylaryl radicals, wherein the aryl portion is optionally substituted with at least one substituent, which may be identical or different; and heterocyclic radicals;

R$_8$ and R$_9$ cannot simultaneously represent either an aromatic radical or a heteroaromatic radical;

R$_{10}$, which may be identical or different, is chosen from a hydrogen atom; linear and branched, optionally substituted C$_1$-C$_8$ alkyl radicals; optionally substituted C$_6$-C$_{30}$ aryl radicals; amino radicals; amino radicals substituted with at least one substituent chosen from linear and branched C$_1$-C$_4$ alkyl radicals, optionally bearing at least one hydroxyl radical; hydroxyl radicals; linear and branched C$_1$-C$_8$ alkoxy radicals, optionally bearing at least one substituent chosen from hydroxyl radicals and C$_1$-C$_4$ alkoxy radicals; and halogen atoms;

X is chosen from a nitrogen atom and a carbon atom;

n is equal to 0 when X is a nitrogen atom, and 1 when X is a carbon atom;

n' is equal to 4;

A$_1$ is chosen from amino radicals; amino radicals substituted with at least one substituent, which may be identical or different, chosen from linear and branched C$_1$-C$_8$ alkyl radicals, optionally bearing at least one substituent chosen from a hydroxyl radical and N$^+$(R$_{11}$)$_2$ ammonium radicals, wherein R$_{11}$, which may be identical or different, is chosen from optionally substituted C$_1$-C$_8$ alkyl radicals; and C$_6$ aryl radicals, which is optionally substituted; and (2) chromophores of formula (V) below and, where appropriate, tautomeric forms thereof:

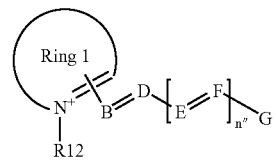
(V)

wherein:

B, D, E and F, which may be identical or different, are each chosen from a nitrogen atom and groups C—R$_{13}$, wherein R$_{13}$, which may be identical or different, is chosen from a hydrogen atom, C$_1$-C$_8$ alkyl radicals which are optionally substituted; linear and branched C$_1$-C$_4$ alkoxy radicals; amino radicals; amino radicals substituted with at least one substituent, which may be identical or different, chosen from linear and branched C$_1$-C$_4$ alkyl radicals, optionally bearing at least one hydroxyl group; optionally substituted C$_6$ aryl radicals; and optionally substituted 5- to 12-membered heteroaryl radicals;

n''=0 or 1;

G represents Ring 4 or residues:

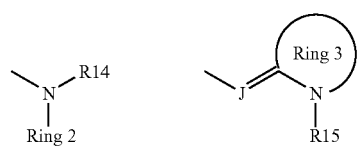

wherein:

$R_{12}$ and $R_{15}$, which may be identical or different, are each chosen from linear and branched, optionally substituted $C_1$-$C_8$ alkyl radicals and optionally substituted benzyl radicals;

$R_{14}$ is chosen from a hydrogen atom, $C_1$-$C_8$ alkyl radicals, which are optionally substituted; optionally substituted $C_6$ aryl radicals; and optionally substituted $C_2$-$C_{12}$ heteroaryl radicals;

J is chosen from a nitrogen atom and groups C—$R_{16}$; wherein $R_{16}$, which may be identical or different, is chosen from a hydrogen atom, $C_1$-$C_8$ alkyl radicals which are optionally substituted; linear and branched $C_1$-$C_4$ alkoxy radicals; amino radicals; amino radicals substituted with at least one substituent, which may be identical or different, chosen from linear and branched $C_1$-$C_4$ alkyl radicals, optionally bearing at least one hydroxyl group; optionally substituted $C_6$ aryl radicals; and optionally substituted 5- to 12-membered heteroaryl radicals;

Ring 1 is chosen from 5- to 12-membered heteroaromatic radicals, bearing at least one cationic charge on a nitrogen atom and optionally comprising at least one other hetero atom chosen from nitrogen, oxygen and sulfur; wherein the radicals are optionally substituted with at least one substituent chosen from linear and branched, substituted and unsubstituted $C_1$-$C_8$ alkyl radicals; linear and branched, substituted and unsubstituted $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; $C_5$-$C_6$ aromatic radicals; a hydroxyl radical; linear and branched $C_1$-$C_8$ alkoxycarbonyl radicals; nitro radicals; cyano radicals; linear and branched $C_1$-$C_{12}$ alkylsulfonamido radicals (alkyl-$SO_2$—NH—); and linear and branched $C_1$-$C_{12}$ alkylsulfamoyl radicals (alkyl-N H—$SO_2$—);

Ring 2 is chosen from $C_6$-$C_{12}$ aromatic radicals; 5- to 12-membered heteroaromatic radicals, comprising at least one hetero atom chosen from nitrogen, oxygen and sulfur; wherein the radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; (hetero)aromatic radicals; and a hydroxyl radical;

Ring 3 is chosen from 5- and 6-membered heteroaromatic radicals comprising at least one hetero atom chosen from nitrogen, oxygen and sulfur; wherein the radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl group; $C_5$-$C_6$ aromatic radicals; a hydroxyl radical; linear and branched $C_1$-$C_8$ alkoxycarbonyl radicals; a nitro radical; a cyano radical; linear and branched $C_1$-$C_{12}$ alkylsulfonamido radicals (alkyl-$SO_2$—NH—); and linear and branched $C_1$-$C_{12}$ alkylsulfamoyl radicals (alkyl-NH—$SO_2$—); and Ring 4 is chosen from $C_6$-$C_{12}$ aromatic radicals; 5- to 12-membered heteroaromatic radicals, comprising at least one hetero atom chosen from nitrogen, oxygen and sulfur; wherein the heteroaromatic radicals are optionally substituted with at least one substituent chosen from linear and branched $C_1$-$C_8$ alkyl radicals; linear and branched $C_1$-$C_8$ alkoxy radicals; amino radicals; amino radicals substituted with at least one substituent, which may be identical or different, chosen from linear and branched $C_1$-$C_8$ alkyl radicals, optionally bearing at least one hydroxyl radical; (hetero)aromatic radicals; and a hydroxyl radical;

provided that when n" is 1 and G represents a ring, then B, D, E and F cannot simultaneously represent a nitrogen atom; and that when n" is 0 and G represents a ring, then B and D do not simultaneously represent a nitrogen atom.

16. The composition according to claim 1, wherein the at least one mixed dye comprises at least one chromophore chosen from carbonyl compounds.

17. The composition according to claim 16, wherein the at least one chromophore chosen from carbonyl compounds is a radical derived from dyes of acridones, benzoquinones, anthraquinones, naphthoquinones, benzanthrones, anthranthrones, pyranthrones, pyrazolanthrones, pyrimidinoanthrones, flavanthrones, idanthrones, flavones, (iso)violanthrones, isoindolinones, benzimidazolones, isoquinolinones, anthrapyridones, pyrazoloquinazolones, perinones, quinacridones, quinophthalones, indigoids, thioindigos, naphthalimides, anthrapyrimidines, diketopyrrolopyrroles and coumarins.

18. The composition according to claim 16, wherein the at least one chromophore chosen from carbonyl compounds is a radical derived from dyes of formula (VI) below:

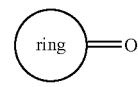

wherein: the ring represents a 5- or 6-membered ring, at least one of the ring members of which is optionally replaced with at least one entity chosen from oxygen, nitrogen and sulphur atoms and additional carbonyl function groups; wherein the ring is optionally substituted with at least one substituent chosen from optionally substituted linear and branched $C_1$-$C_8$ alkyl radicals; a hydroxyl radical; halogen atoms; and nitro, cyano, amino and alkylamino radicals; wherein the ring is optionally fused with at least one $C_6$ aromatic ring, this or these ring(s) themselves possibly being fused with at least one aromatic ring, at least one of the carbon atoms of which is optionally replaced with at least one hetero atom chosen from oxygen, nitrogen and sulfur.

19. The composition according to claim 1, wherein the at least one linker is cationic or non-cationic.

20. The composition according to claim 1, wherein the at least one linker is chosen from a linear and branched $C_1$-$C_{20}$ hydrocarbon-based chains, wherein at least one of the carbon atoms of the chain can be replaced with at least one entity chosen from hetero atoms and saturated and unsaturated 5- and 6-membered heterocycles, wherein the hydrocarbon-based chains are possibly unsaturated or comprise at least one arylene radical; arylene radicals; divalent terephthalamide radicals; and divalent and trivalent radicals.

21. The composition according to claim 1, wherein the at least one mixed dye is present in an amount ranging from 0.001% to 20% by weight, relative to the total weight of the composition.

22. The composition according to claim 21, wherein the at least one mixed dye is present in an amount ranging from 0.005% to 10% by weight, relative to the total weight of the composition.

23. The composition according to claim 22, wherein the at least one mixed dye is present in an amount ranging from 0.01% to 5% by weight, relative to the total weight of the composition.

24. The composition according to claim 1, further comprising at least one additional direct dye other than the at least one mixed dye.

25. The composition according to claim 24, wherein the at least one additional direct dye is present in an amount ranging from 0.001% to 10% by weight, relative to the total weight of the composition.

26. The composition according to claim 1, further comprising at least one oxidation base chosen from para-phenylenediamines, bis(phenyl)alkylenediamines, para-aminophenols, ortho-aminophenols, heterocyclic bases, and addition salts thereof.

27. The composition according to claim 1, further comprising at least one coupler chosen from meta-phenylenediamines, meta-aminophenols, meta-diphenols, naphthalene-based couplers, heterocyclic couplers, and addition salts thereof.

28. The composition according to claim 26, wherein the at least one oxidation base is present in an amount ranging from 0.001% to 10% by weight, relative to the total weight of the composition.

29. The composition according to claim 27, wherein the at least one coupler is present in an amount ranging from 0.001% to 10% by weight, relative to the total weight of the composition.

30. The composition according to claim 1, further comprising at least one oxidizing agent.

31. The composition according to claim 30, wherein the at least one oxidizing agent is chosen from hydrogen peroxide, alkali metal and alkaline-earth metal peroxides, urea peroxide, alkali metal bromates, ferricyanides, persalts, and enzymes.

32. The composition according to claim 1, wherein the composition has a pH ranging from 8 to 11.

33. A process for dyeing keratin fibers, comprising:
a) applying to wet or dry fibers, optionally in the presence of at least one oxidizing agent, at least one dye composition comprising, in a medium that is suitable for dyeing keratin fibers, at least one mixed dye comprising at least two chromophores, wherein at least one of the chromophores is chosen from cyclic azine and (hetero)aromatic nitro compounds, optionally associated with at least one chromophore chosen from methine and carbonyl compounds, wherein the at least two chromophores are linked together via at least one linker that stops delocalization of the electrons of each of the chromophores;
with the following exceptions:
the dye composition is not a composition comprising a mixed dye comprising two chromophores, one of which is a benzene nitro compound and the other an anthraquinone or benzene nitro compound; wherein the two chromophores are connected by a nitrogen atom through a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals, and
the dye composition does not comprise compounds of the following formulae:

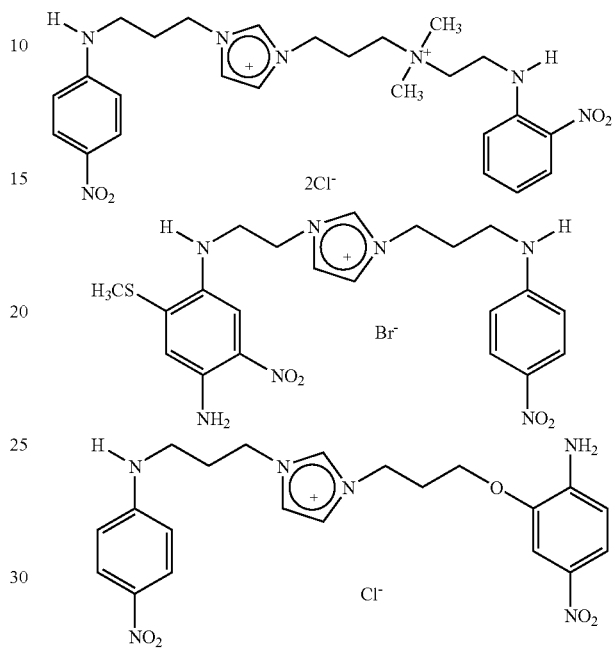

b) leaving the at least one dye composition on the fibers for a time that is sufficient to obtain the desired coloration;
c) optionally rinsing the fibers;
d) washing and rinsing the fibers; and
e) drying the fibers or leaving the fibers to dry.

34. The process according to claim 33, wherein the keratin fibers are human keratin fibers.

35. A multi-compartment device comprising,
at least one first compartment comprising,
at least one dye composition comprising, in a medium that is suitable for dyeing keratin fibers, at least one mixed dye comprising at least two chromophores, wherein at least one of the chromophores is chosen from cyclic azine and (hetero)aromatic nitro compounds, optionally associated with at least one chromophore chosen from methine and carbonyl compounds, wherein the at least two chromophores are linked together via at least one linker that stops delocalization of the electrons of each of the chromophores; with the following exceptions:
the dye composition is not a composition comprising a mixed dye comprising two chromophores, one of which is a benzene nitro compound and the other an anthraquinone or benzene nitro compound; wherein the two chromophores are connected by a nitrogen atom through a linker comprising an alkyl radical optionally interrupted by a nitrogen atom bearing one or two radicals chosen from hydrogen, $C_1$-$C_4$ alkyl radicals, and $C_1$-$C_4$ hydroxyalkyl radicals, and
the dye composition does not comprise compounds of the following formulae:

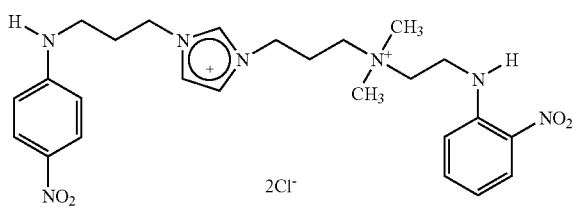

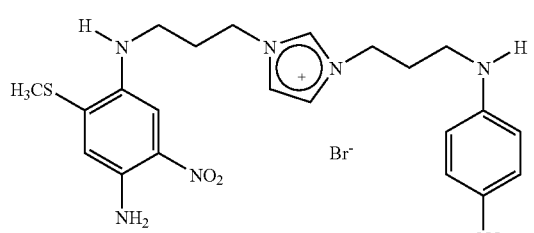

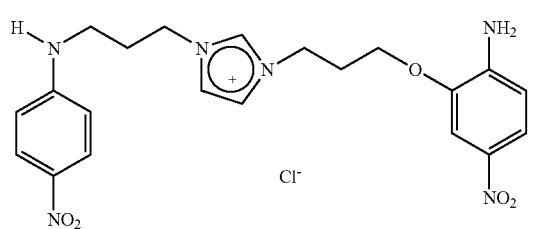

optionally at least one additional direct dye different from the at least one mixed dye, optionally at least one oxidation base, and optionally at least one coupler; and at least one second compartment comprising at least one oxidizing agent.

36. A mixed dye and addition salts thereof comprising at least two different chromophores, wherein at least one of the chromophores is chosen from cyclic azine and (hetero) aromatic nitro compounds, optionally associated with at least one chromophore chosen from methine and carbonyl compounds, wherein the at least two different chromophores are linked together via at least one linker that stops delocalization of the electrons of each of the chromophores;

with the following exceptions, the mixed dye is not a mixed dye having two chromophores, one of which is a benzene nitro compound and the other an anthraquinone or benzene nitro compound; wherein the two chromophores are connected by a nitrogen atom through a linker comprising an alkyl radical optionally interrupted by a nitrogen atom carrying one or two radicals chosen from hydrogen, $C_1$-$C_4$ alkyl radicals and $C_1$-$C_4$ hydroxyalkyl radicals, and the mixed dye is not chosen from compounds of the following formulae:

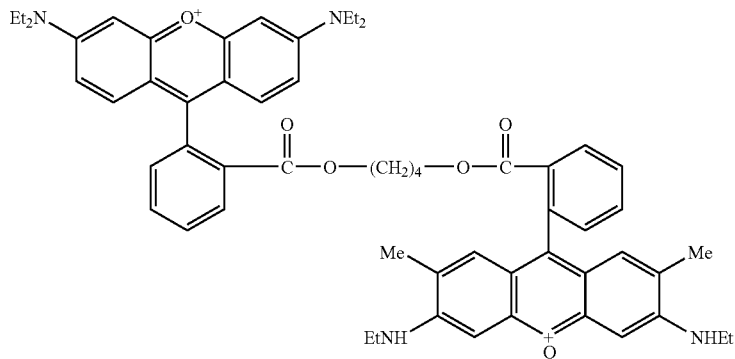

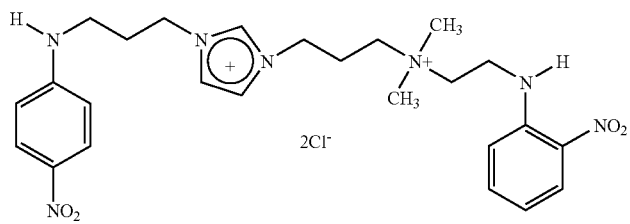

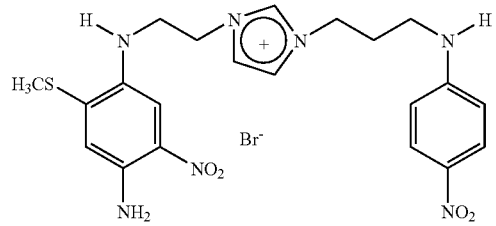

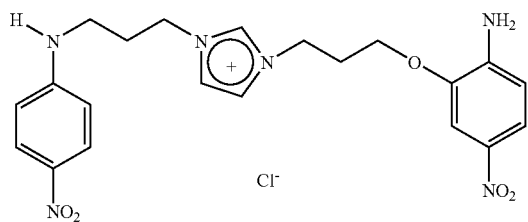

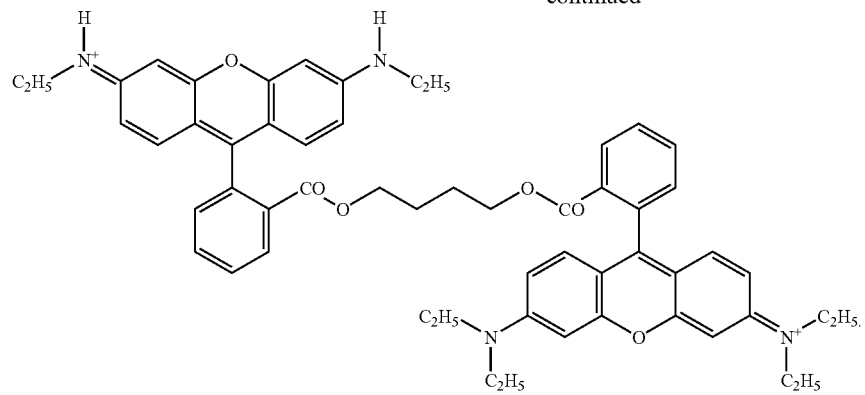
37. A mixed dye according to claim 36, wherein the mixed dye is chosen from compounds corresponding to the following formulae and addition salts thereof:
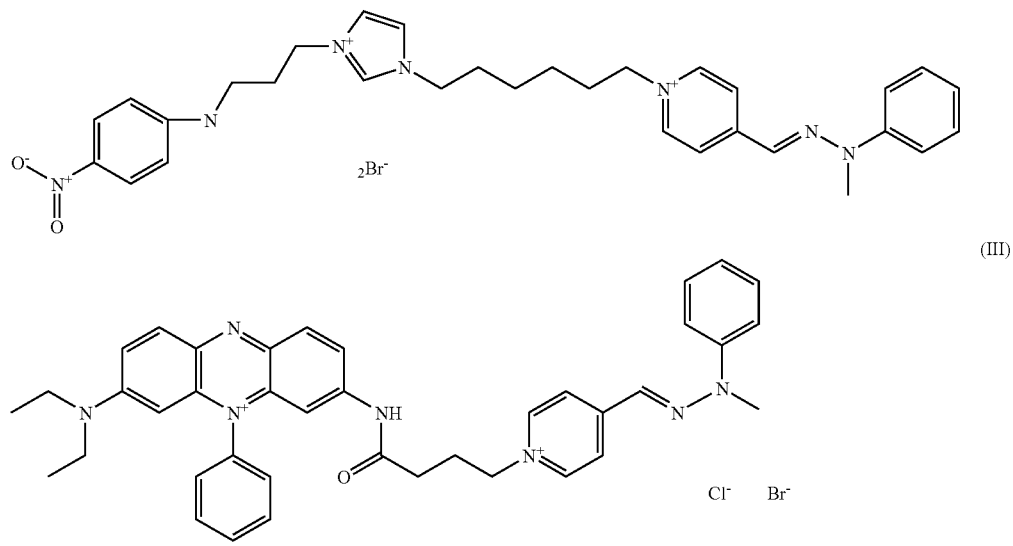
(III)
* * * * *